United States Patent
Shvartsman

(10) Patent No.: US 11,631,477 B2
(45) Date of Patent: Apr. 18, 2023

(54) SYSTEM AND METHOD FOR AUTHENTICATED EXCHANGE OF BIOSAMPLES

(71) Applicant: Dmitry Shvartsman, Sudbury, MA (US)

(72) Inventor: Dmitry Shvartsman, Sudbury, MA (US)

( * ) Notice: Subject to any disclaimer, the term of this patent is extended or adjusted under 35 U.S.C. 154(b) by 1200 days.

(21) Appl. No.: 16/124,442

(22) Filed: Sep. 7, 2018

(65) Prior Publication Data

US 2019/0180850 A1    Jun. 13, 2019

Related U.S. Application Data

(60) Provisional application No. 62/555,353, filed on Sep. 7, 2017.

(51) Int. Cl.
| | |
|---|---|
| *G16H 10/40* | (2018.01) |
| *C12Q 1/6869* | (2018.01) |
| *A61B 10/00* | (2006.01) |

(52) U.S. Cl.
CPC .......... *G16H 10/40* (2018.01); *C12Q 1/6869* (2013.01); *A61B 10/0096* (2013.01)

(58) Field of Classification Search
CPC ... G16H 10/40; C12Q 1/6869; A61B 10/0096
See application file for complete search history.

(56) References Cited

U.S. PATENT DOCUMENTS

| | | |
|---|---|---|
| 5,413,908 A | 5/1995 | Jeffreys |
| 6,297,006 B1 | 10/2001 | Drmanac et al. |
| 6,833,242 B2 | 12/2004 | Quake et al. |
| 7,008,771 B1 | 3/2006 | Schumm et al. |
| 9,892,460 B1 * | 2/2018 | Winklevoss et al. |

(Continued)

FOREIGN PATENT DOCUMENTS

| | | |
|---|---|---|
| WO | WO2016154254 A1 | 9/2016 |
| WO | WO2017024071 A1 | 2/2017 |

(Continued)

OTHER PUBLICATIONS

A. Ekblaw et al., "A Case Study for Blockchain in Healthcaare: 'MedRec' Prototype for Electronic Health Records and Medical Research Data", White Paper, Aug. 2016, pp. 1-13, IEEE.

(Continued)

*Primary Examiner* — Michael Tomaszewski
*Assistant Examiner* — William T. Monticello
(74) *Attorney, Agent, or Firm* — Intrinsic Law Corp.

(57) ABSTRACT

The present disclosure relates to identifying and authenticating samples of biological material such as human tissue samples, especially when such samples are passed from one entity, institution or holding bank to another. In some aspects, a sample Exchange acts as a bio hub in a bio exchange environment, and receives biosamples and associated data from one or more sample collection entities. The Exchange generates and associates a trusted and unique genetic code (UGC) based on the genetic content of a sample, which is carried forward to subsequent sample users in a chain of transactions in said sample, securely identifying and authenticating a physical and digital asset to avoid mistake or fraud in the transfer of said assets.

8 Claims, 21 Drawing Sheets

(56) References Cited

U.S. PATENT DOCUMENTS

| | | | |
|---|---|---|---|
| 10,002,362 | B1* | 6/2018 | Endress et al. |
| 2013/0096943 | A1* | 4/2013 | Carey et al. |
| 2013/0185096 | A1 | 7/2013 | Giusti et al. |
| 2015/0205929 | A1 | 7/2015 | Brama |
| 2016/0072800 | A1* | 3/2016 | Soon-Shiong et al. |
| 2016/0140303 | A1 | 5/2016 | Esrailian et al. |
| 2016/0275308 | A1 | 9/2016 | Hubaux et al. |
| 2018/0082043 | A1 | 3/2018 | Witchey et al. |
| 2018/0130050 | A1* | 5/2018 | Taylor et al. |
| 2018/0173203 | A1 | 6/2018 | Freer et al. |

FOREIGN PATENT DOCUMENTS

| | | |
|---|---|---|
| WO | WO2017163090 A1 | 9/2017 |
| WO | WO2017194976 A1 | 11/2017 |

OTHER PUBLICATIONS

M. Schoner et al., "Blockchain Technology in the Pharmaceutical Industry", Frankfurt School Blockchain Center Working Paper, Jul. 2017, pp. 1-9, FSBC, Germany.

M. Benchoufi et al., "Blockchain Technology for Improving Clinical Research Quality", Benchoufi and Ravaud Trials, 2017, pp. 1-5, 18:335, BioMed Central.

A. Ackerman Shrier et al., "Blockchain and Health IT: Algorithms, Privacy, and Data", White Paper, Aug. 8, 2016, pp. 1-14.

IBM, "Blockchain: The Chain of Trust and its Potential to Transform Healthcare—Our Point of View", White Paper, Aug. 8, 2016, pp. 1-12, IBM, Bethesda, MD.

J.E. Litton et al., "Europe Biobank Week", Abstract Book, Aug. 22, 2016, pp. 1-277.

S. Taylor et al., "Distributed Ledger Technology: Beyond Block Chain", A report by the UK Government Chief Scientific Adviser—Mark Walport, 2016, pp. 1-88, Government Office for Science, London, U.K.

IBM, "Healthcare Rallies for Blockchains, Keeping Patients at the Center", Executive Report, Dec. 2016, pp. 1-24, IBM Corporation, Somers, NY, USA.

T.Khurana, "Sample Patent Landscape Study—Blockchain", Jan. 2017, pp. 1-27, IIPRD, India.

J. Bresnick, "Kaiser Permanente Expands Precision Medicine Biobanking Effort", Analytics in Action News, Apr. 15, 2016, https://healthitanalytics.com/.

National Institute of Standards and Technology, "Background Information Regarding Short Tandem Repeats and DNA Typing", STRBase (SRD-130), https://strbase.nist.gov/intro.htm, Jul. 5, 2007, U.S. Department of Commerce.

M. Molteni, "Moving Patient Data Is Messy, But Blockchain Is Here to Help", https://www.wired.com/2017/02/moving-patient-data-messy-blockchain-help/, Feb. 1, 2017, Conde Nast.

Health IT Consultant Staff, "NIH Awards Mayo Clinic $142M to Create Biobank for Precision Medicine Initiative", https://hitconsultant.net/2016/05/27/34153/, May 27, 2016, HIT Consultant Media.

A. Dubovitskaya, MS, "Secure and Trustable Electronic Medical Records Sharing Using Blockchain", AMIA Annual Symposium Proceedings Archive, Aug. 2, 2017, pp. 650-659, vol. 2017. American Medical Informatics Association.

* cited by examiner

- CSF1PO
- FGA
- THO1
- TPOX
- VWA
- D3S1358
- D5S818
- D7S820
- D8S1179
- D13S317
- D16S539
- D18S51
- D21S11
- D1S1656
- D2S441
- D2S1338
- D10S1248
- D12S391
- D19S433
- D22S1045

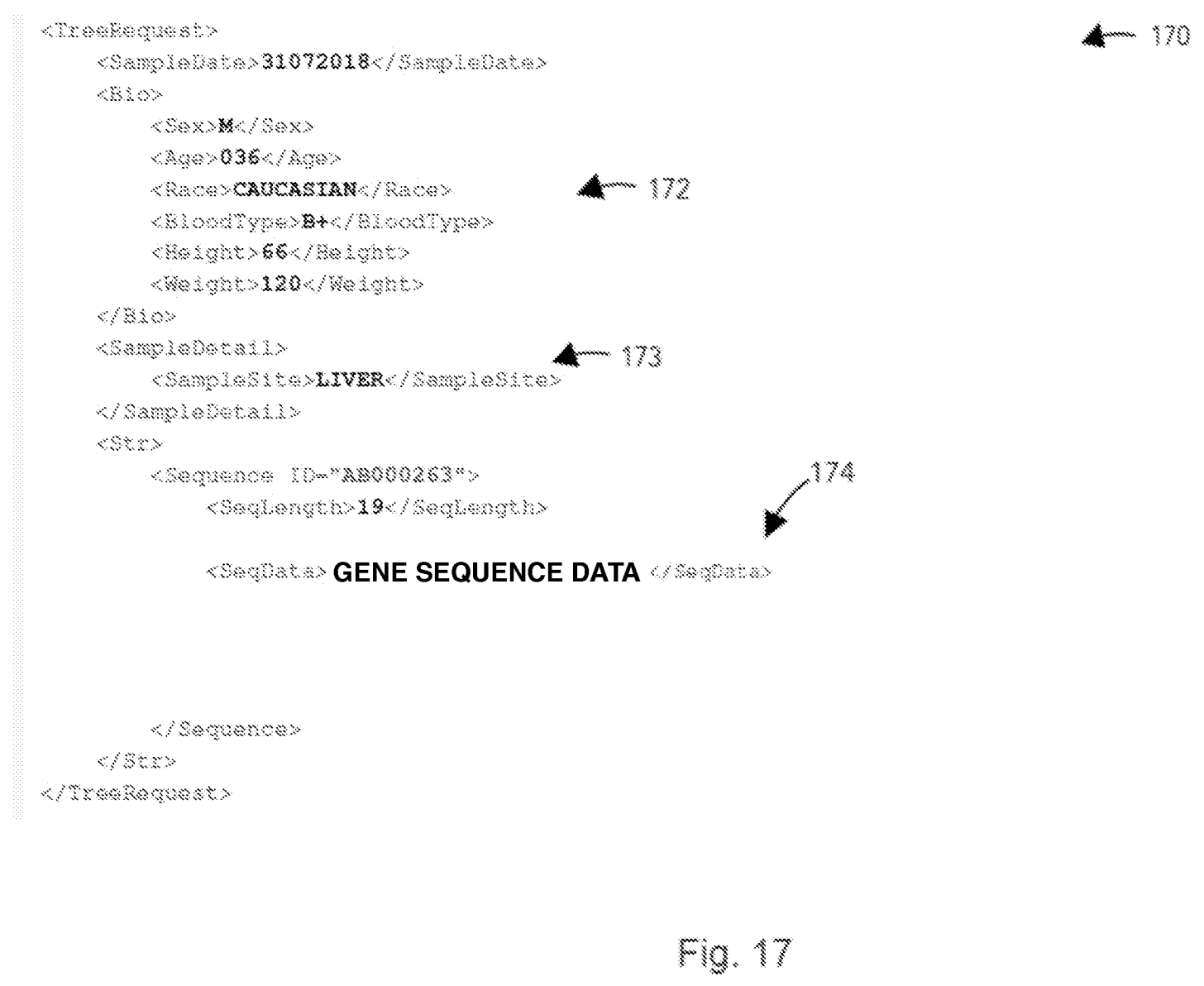

```
<TreeRequest>
    <SampleDate>31072018</SampleDate>          ← 170
    <Bio>
        <Sex>M</Sex>
        <Age>036</Age>
        <Race>CAUCASIAN</Race>                 ← 172
        <BloodType>B+</BloodType>
        <Height>66</Height>
        <Weight>120</Weight>
    </Bio>
    <SampleDetail>
        <SampleSite>LIVER</SampleSite>         ← 173
    </SampleDetail>
    <Str>
        <Sequence ID="AS000263">
            <SeqLength>19</SeqLength>
            <SeqData> GENE SEQUENCE DATA </SeqData>   ← 174
        </Sequence>
    </Str>
</TreeRequest>
```

Fig. 17

SYSTEM AND METHOD FOR AUTHENTICATED EXCHANGE OF BIOSAMPLES

RELATED APPLICATIONS

This application claims priority to U.S. Provisional Application No. 62/555,353, entitled "System and Method for Identifying and Authenticating Biosamples", filed on Sep. 7, 2017, which is hereby incorporated by reference.

TECHNICAL FIELD

The present disclosure relates to identifying and authenticating samples of biological material such as human tissue samples, especially when such samples are passed from one entity, institution, tissue collection or holding biobank to another.

BACKGROUND

Biomaterials such as tissue samples can be taken from a subject at a clinic, lab or other accredited facility, and then stored or transferred to another clinic, lab or facility. It is a known problem that human (or animal) tissue samples being transferred between one entity and another can be subject to accidental or intentional loss, fraud, illegal transfer or misidentification.

Identification of a biosample using DNA tests are possible. Short-tandem repeats (STRs) are a microsatellite sequence comprising a unit of two to thirteen nucleotides repeated many (hundreds) of times in succession on a DNA strand from said sample. For example, a STR named D7S820 is $[GATA]_8$, meaning that the DNA sequence GATA is repeated eight times in a specific location on a specific chromosome of the sample. In the human specimen space, there are 46 chromosomes: 22 autosomal and 2 sex-determining.

As of early 1998, the Federal Bureau of Investigation (FBI), together with other federal institutions, established a "National DNA Index System" and is one part of CODIS—the national level—containing the DNA profiles contributed by federal, state, and local participating forensic laboratories. NDIS was implemented in October 1998. All 50 states, the District of Columbia, the federal government, the U.S. Army Criminal Investigation Laboratory, and Puerto Rico participate in NDIS.

The DNA Identification Act of 1994 (42 U.S.C. § 14132) authorized the establishment of this National DNA Index. The DNA Act specifies the categories of data that may be maintained in NDIS (convicted offenders, arrestees, legal, detainees, forensic [casework], unidentified human remains, missing persons, and relatives of missing persons) as well as requirements for participating laboratories relating to quality assurance, privacy, and expungement.

As of Jan. 1, 2017, Combined DNA Index System (CODIS) with core loci including 20 STRs. This system of identification is used by some law enforcement agencies in support of criminal investigations and prosecutions, and is used in U.S. justice systems' DNA databases. Other countries have similar or differing methods for genetic identification.

Polymerase-chain reactions (PCRs) and specialty equipment can be used to detect the presence of specific STRs in a bio (tissue) sample. Detecting the quantity of STRs in a sample can be achieved by commercially available kits.

FIG. 1 illustrates an example of the above-mentioned CODIS in its original format, used between 1998 and 2016, which included thirteen loci 10, according to the prior art. The figure describes a set of STR names; the sample chromosome number for an unknown person where an appropriate STR is located; a CODIS sample for a known offender is given; and the matching stringency based on population statistics for the specific STR occurrence at the specific chromosome. A new CODIS system requires the detection of twenty STR loci 20, illustrated in FIG. 2, according to the prior art.

In some cases, a clinic or research institution needs specific tissue samples possessing certain origins or characteristics. Such samples can be quite rare or difficult to obtain, and may thus be very costly to acquire. Recipients of such samples are wary of accidental or intentional substitution or confusion in the acquired tissue samples, especially if the samples have traveled long distances, crossed jurisdictional lines, or been handled by many parties on their way from their origin to the acquiring recipient. Means to avoid sample substitution, sample tracking, establishment of custodial chains or misidentification have not been offered to date.

Each tissue sample collection, biobank or commercial entity traditionally operates as a separate unit, with its own sample tracking, coding and coordination procedures. In the US, for example, the NIH-based Cooperative Human Tissue Network (CHIN) exists, based at the National Cancer Institute (NCI) that provides tissue samples for a fee, having its own certification and sample labeling procedures. Numerous academic and commercial biospecimen collections exists in the world, but there is no uniform or trusted procedure for tracking and exchange of samples.

This invention seeks to address the problem of identifying or authenticating any given biosample to avoid the above problem.

Summary

One embodiment is directed to a method for secure transactions in a biosample, comprising the identification of a physical asset comprising said biosample; obtaining information regarding said biosample from a provider of said biosample; encoding of information regarding said biosample into a corresponding sample data set; interrogating said biosample using a sequencing machine to generate a short tandem repeat (STR) code corresponding to said biosample; generating a digital asset or TReE ID in the present context, uniquely corresponding to said physical asset comprised of a unique genetic code (UGC) based at least on said STR and said sample data set or other data assignable to the physical sample such as a sample serial number; recording said UGC into a secure data store; generating a UGC-codified hash using a public-private key method; encoding, recording or writing said digital asset into a first block of a blockchain; brokering, in an exchange platform, a transaction in both the physical asset and its corresponding digital asset between a first party who holds rights in said physical and digital assets and a second party who intends to take the rights in said physical and digital assets following the transaction; and encoding said transaction, following its completion, into a second block of said blockchain.

Another embodiment is directed to an architecture for secure transaction in a biosample, comprising a genetic testing apparatus for interrogating a physical asset of said biosample to output a unique short tandem repeat (STR)

code corresponding to said biosample; a secure network of servers, configured and arranged to exchange encoded data in signals passed along one or more communication pathways coupling said servers; one or more servers coupled to said network being configured and arranged to receive a sample data set describing said biosample and to receive said STR code, register said sample data set and STR code into a data store coupled to the first server, and process said STR code and said sample data set to generate a digital asset comprising a unique genetic code (UGC) corresponding to said biosample; and a wide area network interface coupled to said network configured and arranged to provide access to at least a first and second user and further configured and arranged to broker a transaction between said first and second users in said physical and digital assets. Additional blockchain blocks may be created encoding each step in the process for exchanging the sample and assets.

Generally stated, one or more embodiments are directed to a process for secure transactions in a biosample, comprising (1) registration of a biosample, including obtaining the sample's STR from a genetic testing or sequencing machine, obtaining chromosomic information regarding the sample, obtaining sample data regarding the sample such as the sample donor's age, type of sample, harvest date, etc., hashing all of the above obtained information regarding the sample, adding a serial number to further identify the sample or any sub-sample thereof, (2) creating a digital asset in the blockchain; (3) listing the sample and its digital asset on an eCommerce exchange; (4) arranging for or brokering an exchange of the physical asset from a first party to a second party; (6) creating a new block in the blockchain transferring the digital asset from the first to the second party.

BRIEF DESCRIPTION OF THE DRAWINGS

For a fuller understanding of the nature and advantages of the present invention, reference is made to the following detailed description of preferred embodiments and in connection with the accompanying drawings, in which:

FIG. 17 illustrates the use of a sample data set;

DETAILED DESCRIPTION

In an aspect of the invention, a unique genetic code (UGC) is provided and used to identify and authenticate a biosample, for example a sample of human tissue.

Figure 1:
FIGS. 1 and 2 illustrate STR loci according to various CODIS requirements according to the prior art.
Figure 2:
Figure 3:
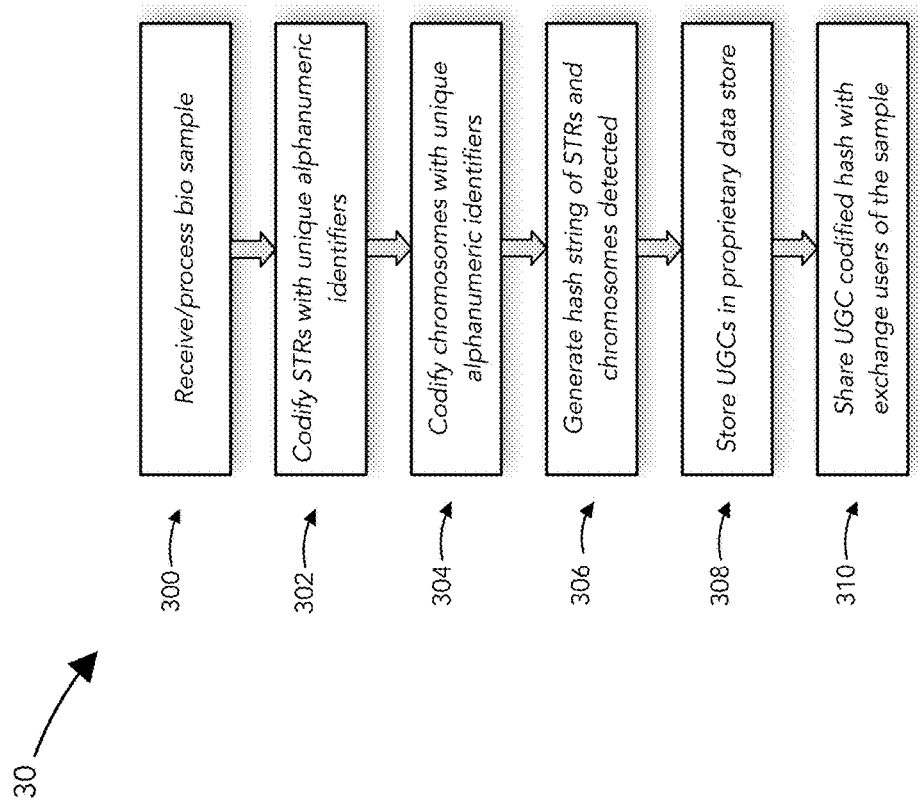
FIG. 3 illustrates an exemplary set of steps in achieving a unique genetic coding (UGC) and processing information relating to the same.

One embodiment includes a system and method for generating and using a unique genetic code (UGC) as illustrated in FIG. 3. The figure outlines a process 30 including some steps of the present method, which those skilled in the art will understand can be modified, combined or further split to suit a given need.

At 300, a sample collection entity, described below, receives and/or processes a biosample from a donor. At 302, STRs are encoded with unique alphanumeric identifiers. At 304, chromosomes are codified with unique alphanumeric identifiers. At 306, a hash string is generated corresponding to detected STRs and chromosomes of said sample. At 308, unique genetic codes (UGCs) are generated and stored in a data storage unit. And, at 310, the UGCs are hashed and shared with users of an exchange as explained further herein.

Figure 4:
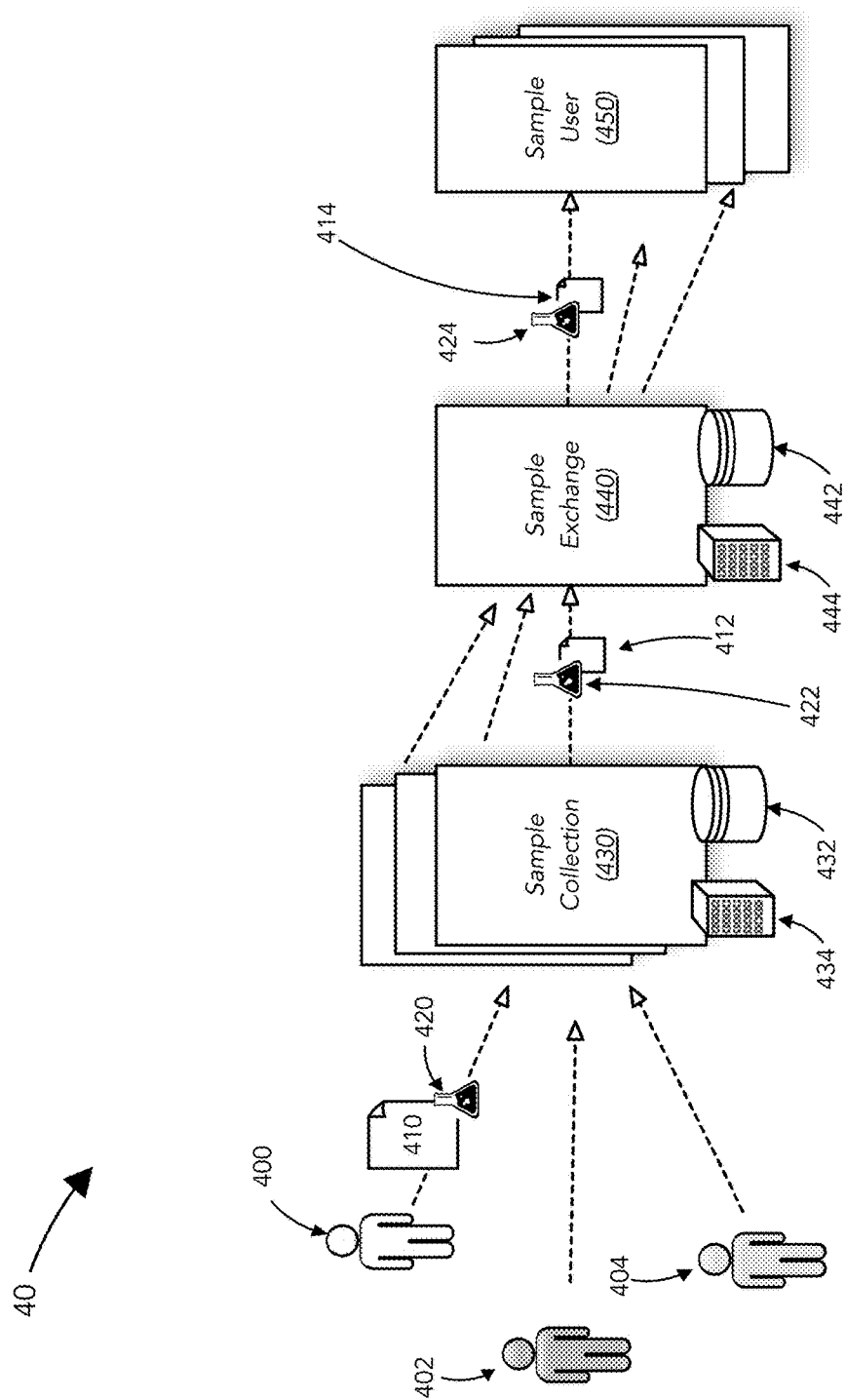
FIG. 4 illustrates an architecture and system, along with steps used to practice the present invention.

FIG. 4 illustrates a sample collection architecture 40 in accordance with one or more embodiments of this invention. A patient, subject or donor 400, 402, 404 (generally, "donor" 400) presents at a clinic, laboratory, office or similar facility for collection of biosamples (generally, "sample collection entity") 430. The sample collection entity 430 is preferably licensed, equipped and qualified to take biosamples such as human tissue samples from a patient, subject or donor. The sample collection entity is also preferably licensed, equipped and qualified to store and log and report the collected samples or specimens as called for by law and/or as needed for the present purposes. The sample collection entity is also preferably able to competently perform certain initial processing, preservation and sample as well as data processing steps as will be discussed below.

A biosample 420, for example but not limited to a human tissue sample, is taken from the donor 400. A record 410 of the donation of the sample is made and kept by the sample collection entity in accordance with any necessary record retention policies, including regulatory or industry standards for keeping of such records. The transfer of certain information in accordance with this invention may be compliant with U.S. federal requirements such as the Health Insurance Portability and Accountability Act (HIPAA). The sample collection entity 430 preferably has access to a secure sample storage facility 434 that keeps samples 420 in appropriate conditions until needed. Also, sample collection entity 430 preferably has access to a secure document storage facility or data store 432.

This invention is concerned with an exchange for biosamples and information relating thereto. Accordingly, a sample exchange or sample exchange 440 entity is established, including physical facilities, computing hardware, data storage, and data communication units to enable the operation of the same. Sample exchange 440 receives samples 422 and documentation 412 from a sample collection entity 430. Sample exchange 440 may have its own sample storage facility 444 as well as its own data storage facility or database 442. Preferably, the sample exchange 440 operates in an environment 40 connecting and facilitating cooperation between exchange 440 and a plurality of sample collection entities 430. As will be discussed, sample exchange 440 is also in communication with and works to service one or more sample user entities 450, which may be commercial or research entities such as universities, research labs, companies, government agencies and the like. Sample exchange 440 may take in biosamples 422 and provide a listing of such available samples 422 based on information 412 associated with each sample 422. Sample users 450 can then find that biosamples they need are available from exchange 440 and request the same. If available, exchange 440 can deliver a requested sample 424 and information record 414, with assurance of authenticity and identification confirmation of the same, to sample user 450. Also, exchange 440 can go find and fetch needed samples for users 450 on demand based on a request from a user 450. As will be explained, the sample material 420 passes from its donor source 400 to sample collection entity 430, then as sample 422 from sample collection entity 430 to sample exchange entity 440, then as sample 424 from sample exchange 440 to sample user 450. At each step, information associated with the sample accompanies the sample to identify and authenticate the same (420, 412, 414 respectively). The present system and method provide for the use of secure and trusted unique genetic coding (UGC) as part of the infrastructure for avoiding fraud or error in the transmittal of a biosample such as human tissue from its source to its end destination, with the sample exchange 440 playing a key role in the generation and processing of the UGC as a feature of the present trust environment.

In an aspect, the afore-mentioned STR and chromosome data for a given biosample are used as inputs to generate the present sample-specific UGC.

Figure 5:
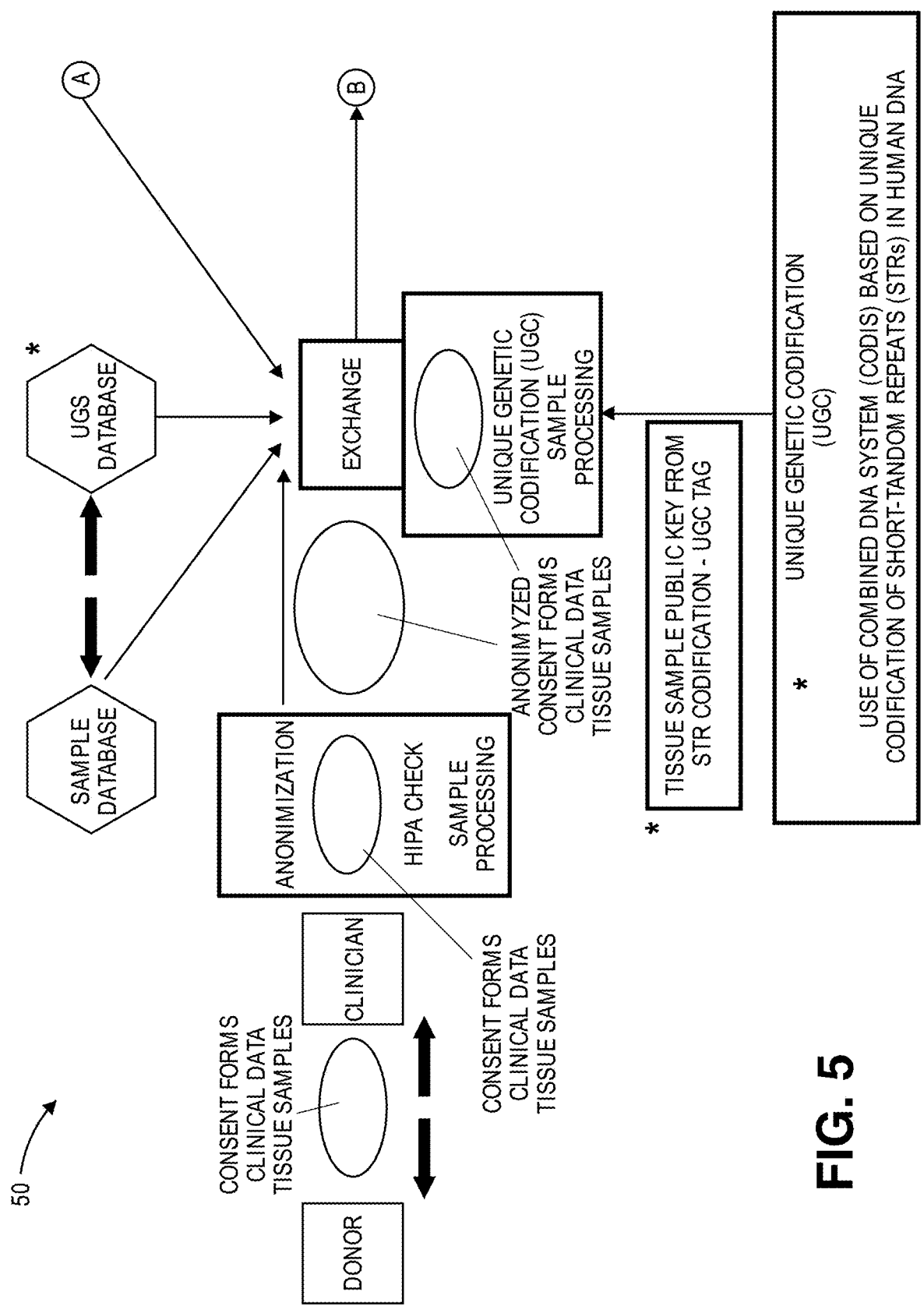
FIG. 5 illustrates an exemplary architecture according to embodiments of the invention.
Figure 5:
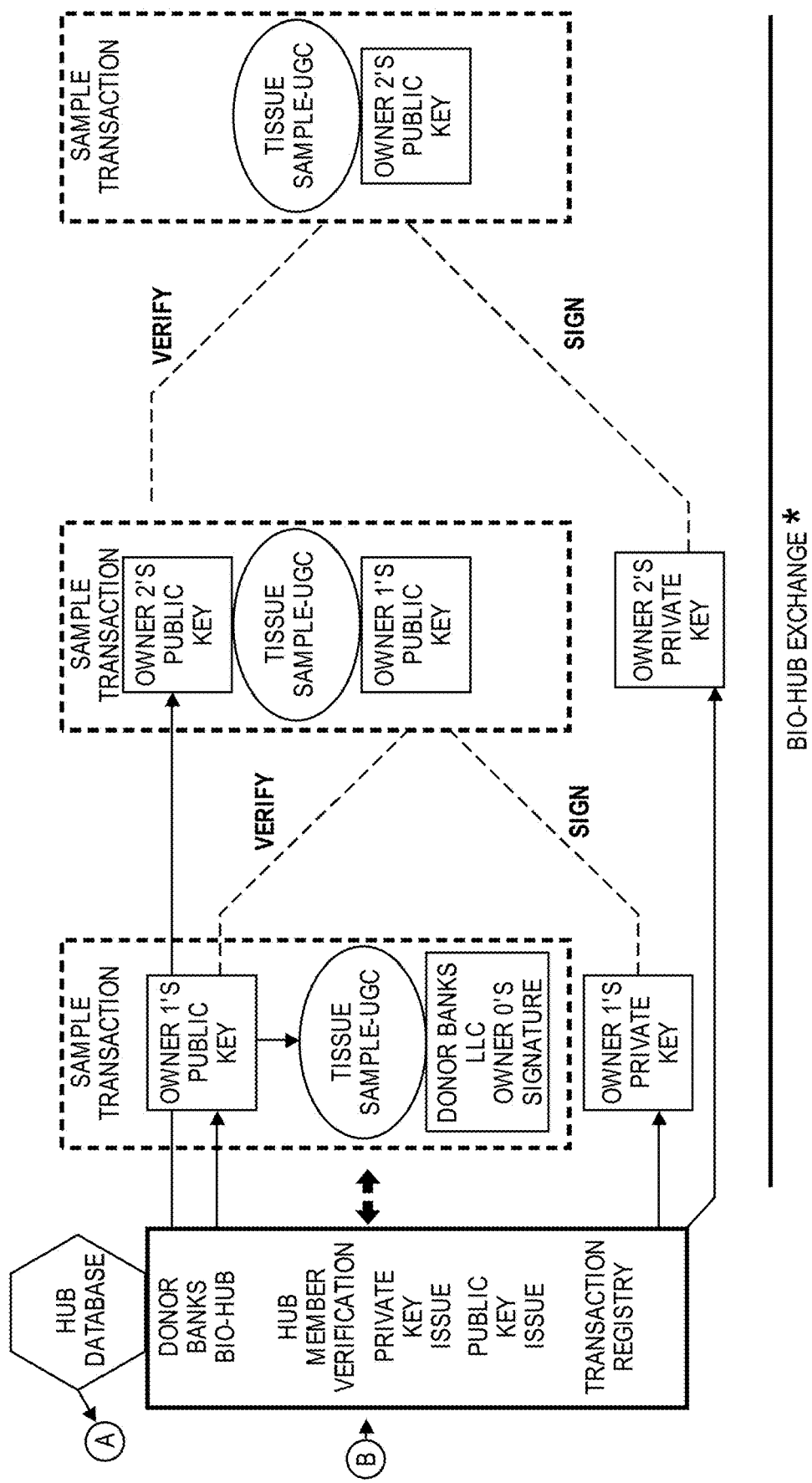

FIG. 5 illustrates how the above parties interact in an embodiment of the invention 50. Specifically, and according to an illustrative embodiment, the donor provides a biosample to a clinician at a sample collection facility. The donor is in turn provided with a consent form to be completed indicating that the donor agrees to provide the biosample. Optionally, other personal identifying information (PII), clinical data, demographic information and so on may also be collected and associated with the collected biosample. In other examples, no PII is collected or retained by the exchange operator. The clinician (generally, sample collection entity) anonymizes the information associated with the sample and the donor so as to retain any necessary anonymity and protect the privacy of the donor as required or agreed under the consent form. An automated system and method can be implemented by the clinician to conform to one or more regulatory set of rules such as HIPAA or other international or national requirements. In addition, the clinician can perform some sample processing to suit a sample storage need or prepare the sample for placement onto the present exchange.

A sample exchange entity (or "Exchange"), which can involve a commercial enterprise, hardware, software and informational infrastructure is then able to transact using the collected specimen or derivative or portion thereof, which also includes data relating to the sample. In one embodiment, the Exchange merely processes digital assets associated with the physical biosample and the physical biosample is at all times held and/or managed by other parties such as a biobank (provider) or other logistic intermediaries. In an alternative embodiment, the Exchange receives a physical biosample from the sample collection entity or biobank and also receives processed or anonymized information (e.g., data) from the collection entity. Preferably, the Exchange deals only with reputable, known and/or trusted clinicians from which appropriate biosamples are sourced. Nonetheless, each biosample is verified by way of its STR and analysis files.

The Exchange generates a unique genetic code (UGC) for the particular sample in question. The UGC and sample are uniquely associated (one-to-one) and a public key is generated from the STR and chromosomal parameters as mentioned above. In this embodiment, the sample includes the physical biosample, corresponding catalog information and associated anonymized documentation. The UGC may comprise a proprietary or standardized code and may use a CODIS or CODIS-based system of codification. As will be discussed further below, the physical biosample is thus uniquely associated with a corresponding digital asset corresponding to that specific biosample or sub-sample thereof, said digital asset comprising a so-called TReE ID by the present applicant and that is written to or encoded into a block of a blockchain.

The Exchange can include or be coupled to a hub (biohub) database containing a plurality of collection or donor banks, corresponding hub member identifications and verification information, as well as private and public keys for use therewith. A transaction registry can also be included in the hub database.

One or more transactions involving a biosample and any documentation associated therewith can then take place using the above digital asset (TReE ID) and sample. For example, a first owner or sample user has the first public key that is applied to the tissue sample that is the subject of the first transaction in said sample. The first owner's private key is used as a means of authenticating a signature. A second owner having a respective second public key and private key can then carry out a second transaction in said sample (or authenticated portion or derivative thereof), and so on. The sample's TReE ID remains the key to uniquely identify and authenticate the sample throughout these transactions in the sample to avoid accidental or intentional misidentification of a sample.

In an aspect, the above-mentioned digital asset and secure keys can be based on scalable web architecture and distributed system, with a distributed data storage system using block chain principles. For example, a block chain open source solution and tools can be employed to create so-called smart contracts between parties in a transaction involving biosamples. Each sample introduced to the present bio hub exchange can be codified with a unique digital asset and be registered into the block chain infrastructure of this architecture. The above-mentioned STR encoding may be further secured using a RSA crypto system or similar encryption methodology.

In an example, the encoding and decoding of the present UGC requires a plurality of digital keys to access the STR table to gain access to the full information regarding a biosample. A first closed access (private) key is stored in the present exchange data store and is used by a purchaser or user entity for decoding the sample information requests from sample users or owners registered with the present bio hub. An open access (public) key is generated for each sample through RSA or similar methods for encryption and is stored in a block chain infrastructure, e.g., as an alphanumeric sequence. Another open access (public) key is used by a purchaser or user entity to identify the user entity party. A sample UGC may be based on CODIS STR tables for a biosample and encoded using RSA or similar methods, and a corresponding digital asset or TReE ID is incorporated into a hash field on the block in said block chain.

For a transaction involving a biosample, a block including the TReE ID key hash is transferred to a new user entity or owner of the sample (e.g., a buyer), and the block is stored with the new user or owner or buyer as well as information identifying the owner. Information regarding the sample and transaction therein can be continuously updated and kept in a block chain wallet or similar means to allow custody and sample tracking in a transparent and secure way. Sample verification can therefore be achieved at any time by a sample owner (transferee) or a regulatory authority by verification of the same in the servers of the Exchange entity.

Figure 6:
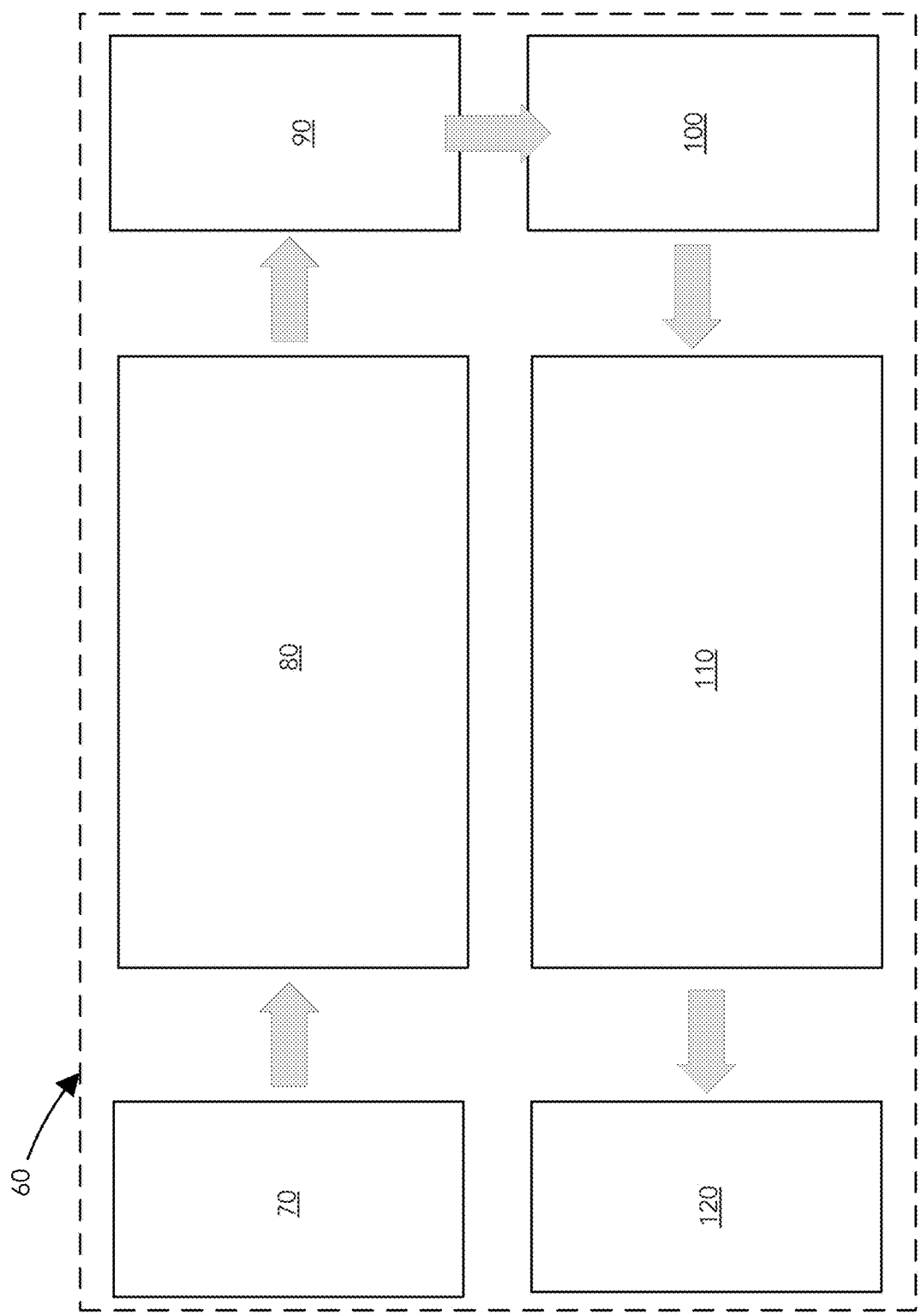
FIG. 6 depicts an overall exemplary architecture and process according to the invention.

FIG. 6 illustrates an exemplary overall architecture and process 60 showing how the various parties to a transaction or event experience the invention. The architecture and process 60 comprises Supplier and Consumer on-boarding 70, Register of samples 80, List in exchange 90, the Exchange described above 100, sample Exchange process using blockchain 110, and final results of the process 120.

Figure 7:
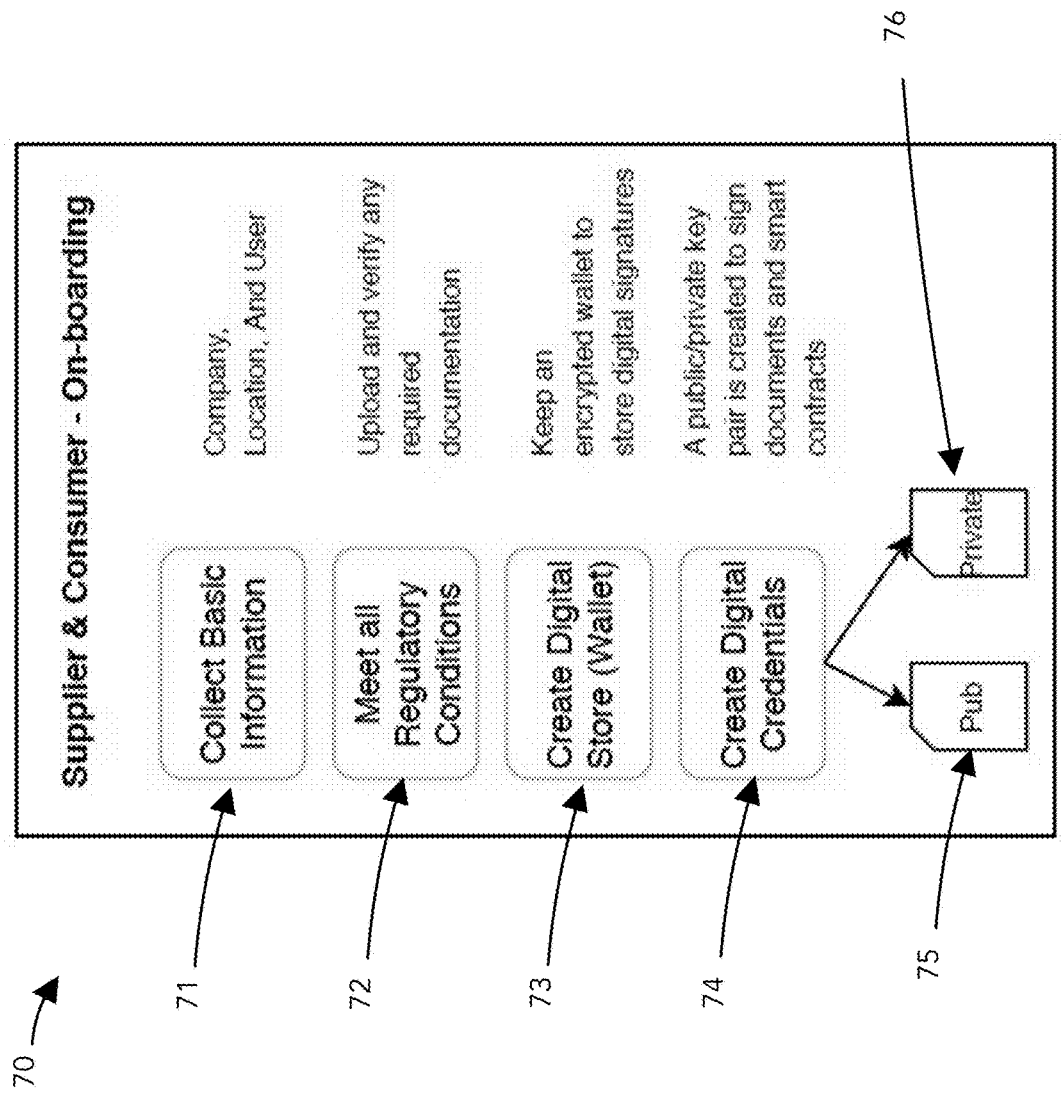
FIG. 7 illustrates user on-boarding.

Referring to FIG. 7, we discuss the Supplier and Consumer on-boarding engine, module and process 70. Here the system and method collect basic consumer information from a user or consumer of the present goods and services at 71. The consumer information can include the name of the consumer, e.g., a company or individual or institution name, the consumer's address and contact information, or other basic information needed to offer the services. The system and method also check with respect to a given transaction whether applicable regulatory requirements have been met at 72. This can include comparison of transaction-specific data against stored or accessible rules encoding one or more laws, regulations, or terms of service, which can be national, local, international or mandated at an institution level.

A digital wallet is created at 73, which can be used to securely store information or data such as digital signatures. Also, digital credentials are generated, which include a consumer's public/private key pair (75, 76) for signing documents, smart contracts or other instruments. It will be seen that the present system and method leverage the above steps for application of the invention using blockchains for best results.

Figure 8:
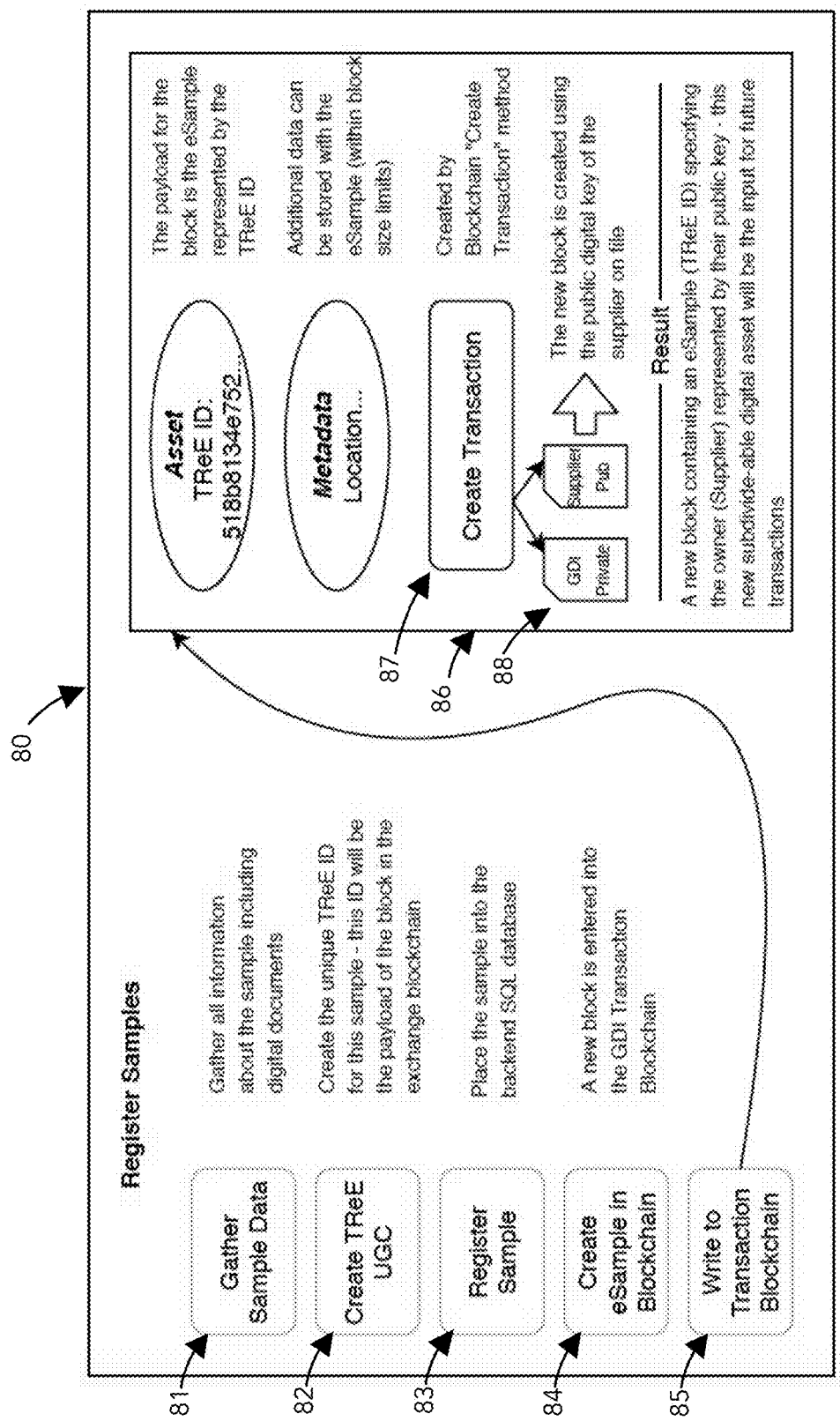
FIG. 8 illustrates registration of biosamples.

FIG. 8 illustrates an exemplary Register Samples engine, module and process 80. The system and method gather sample data regarding a biosample at 81. This collection includes gathering digital documents regarding the sample as previously discussed. A unique digital asset or TReE ID based in part on the UGC is created at 82. The unique identifier will be the payload of the block in the exchange blockchain according to one or more embodiments. We note that the physical processing of a sample (for example, to authenticate physical goods, biosamples, chemicals, etc.) may or may not be performed by the party that runs the present Exchange. In some instances, this party may indeed take on the service to test or authenticate physical assets such as performing gene sequence testing as described earlier to generate a suitable UGC. In other instances, a licensed or trusted third party performs these services, which may require complicated lab equipment in some fields of art.

The sample data is placed at 83 into a database such as a SQL database that may be implemented at the backend of the present system and process. Other data stores and repositories can be used as suitable in a given implementation. A block in the present blockchain is created which represents the sample in question (an electronic sample) and the new block is entered into the present transaction blockchain at 84.

Therefore, this system and method generate a block in a blockchain, shown at 86, which carries or encodes a payload which is the TReE ID electronically representing the biosample (i.e., an electronic sample), as well as related metadata that can be stored and/or transmitted with the electronic sample as appropriate. This can be considered a digital asset corresponding to the physical biosample asset.

The blockchain "create transaction" method 87 causes a unique supplier private/public key pair 88 to be generated. The digital asset is signed with the private key of the (first) owner of record at the time of the transaction using his or her private key and the new (second) owner's public key. The new block described above is thus generated using the public digital key of the supplier on file for the given sample.

Generally, the current examples and preferred embodiments should not be taken as exclusive or exhaustive, nor limiting of the current invention. Rather, they are to be understood as illustrative. Those skilled in the art will appreciate after reviewing this disclosure that other equivalent embodiments can be adopted, which are covered by the scope of this invention as well.

Figure 9:
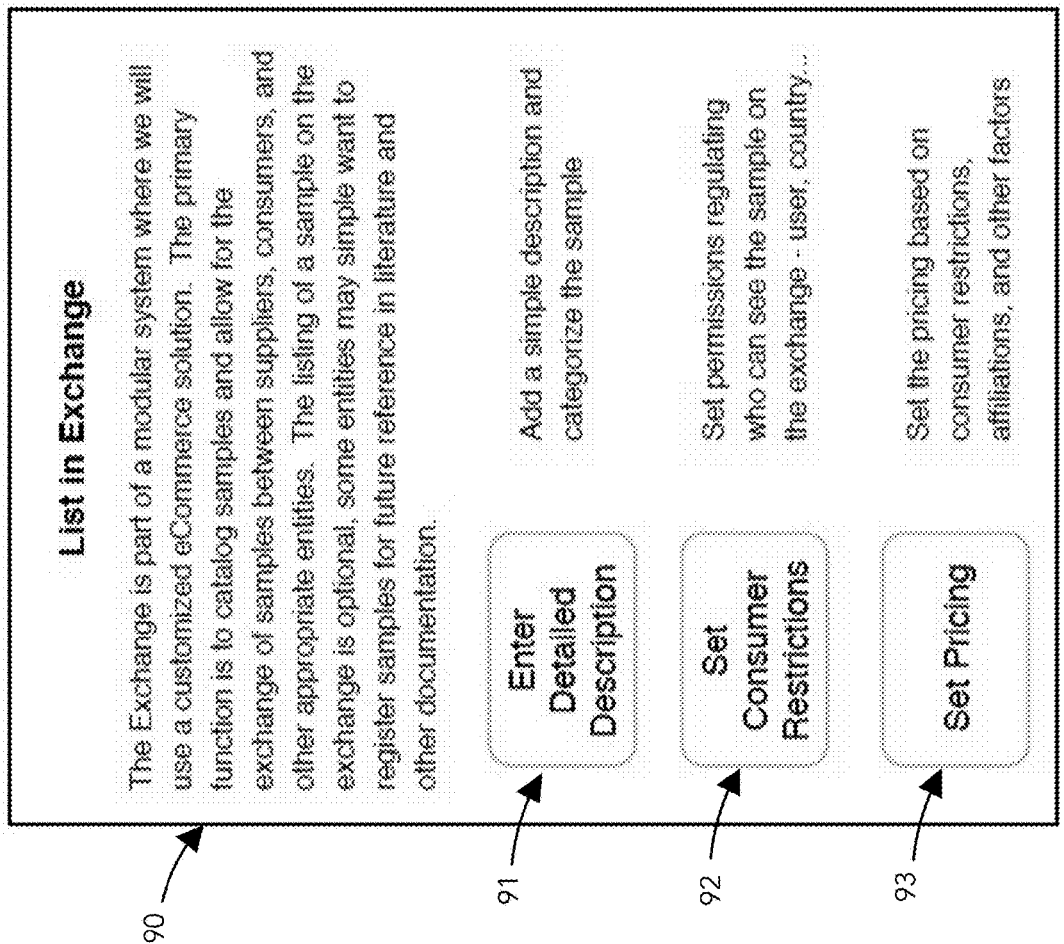
FIG. 9 illustrates listing registered samples into an exchange.

FIG. 9 illustrates an engine, module or process 90 for Listing in an Exchange. The Exchange listing can be managed using an electronic commerce (eCommerce) solution, for example through a Web-based interface according to standard protocols (e.g., IP, HTML, SHTML or similar). In the user interface of the Exchange, and referring to step 91, a party looking for a specimen can add a description of a specimen, search for a specimen by its unique identifier(s), location, or search for a specimen by its characteristics. A party offering a specimen can likewise list it and describe the specimen using one or more identifiers or characteristics. The eCommerce platform can perform some filtering or other access controls based, for example, on the identity of the parties transacting or on the nature of the assets in question. At step 92, the system and method can set consumer/user restrictions as appropriate, which may include who can see and transact in a sample, or may limit the age of such parties, or their geographic location and so on.

Also, pricing for the sample or asset is determined at step 93. This can be done by the provider or seller or owner of a sample, which may include setting a sale price for said sample. The nature of the buyer or asset may determine the pricing, which can be set according to any suitable method. For example, educational institutions may receive free or reduced pricing in an example.

In an aspect, the Exchange may be used to catalog samples (for example, biosamples, but not only limited thereto). The system and method using this Exchange comprehend both physical and digital/electronic assets that are unique and correspond to one another.

Additionally, in an aspect, where the physical asset can and is subdivided (for example, splitting a biosample into two or more sub-samples) the corresponding digital asset(s) can be similarly sub-divided with each child asset (physical or digital) retaining a now-unique child identifier uniquely corresponding thereto. Each sub sample or asset may be treated on its own according to this invention.

Figure 10:
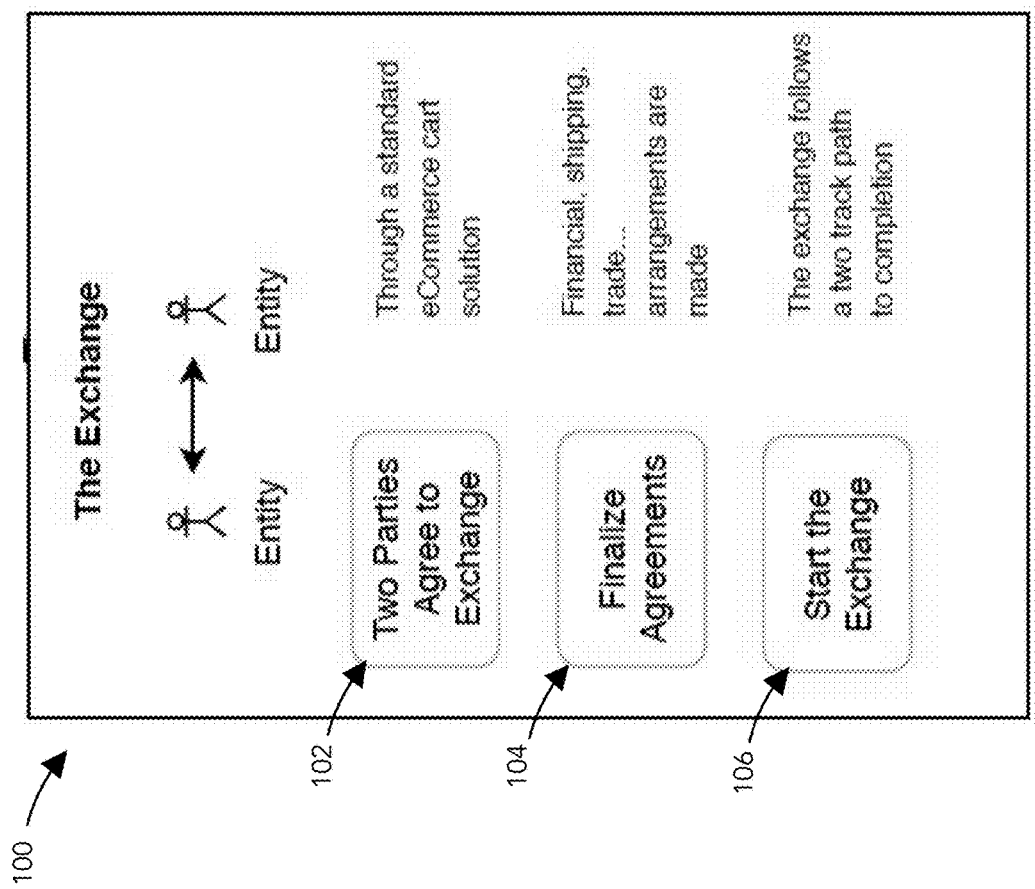
FIG. 10 illustrates the overall operation of the exchange.

FIG. 10 illustrates another view of an Exchange 100 according to the present system and method. Generally, the present transactions are multi-party transactions involving two or more entities as depicted. One entity is typically the owner, holder or provider of the assets of interest, and the other entity is a consumer, customer or acquirer of the same assets. The parties agree to an exchange or transaction at step 102, for example by way of a secure eCommerce platform (e.g., a Web-based portal or site) as described. Various arrangements for exchanging consideration (e.g., funds or other consideration) and for exchanging the assets are made at step 104. The exchange is executed by a two-path method at step 106, which involves transacting both the physical asset and its corresponding electronic or digital asset. The following discussion elaborates on these paths or branches of the transaction.

Figure 11:
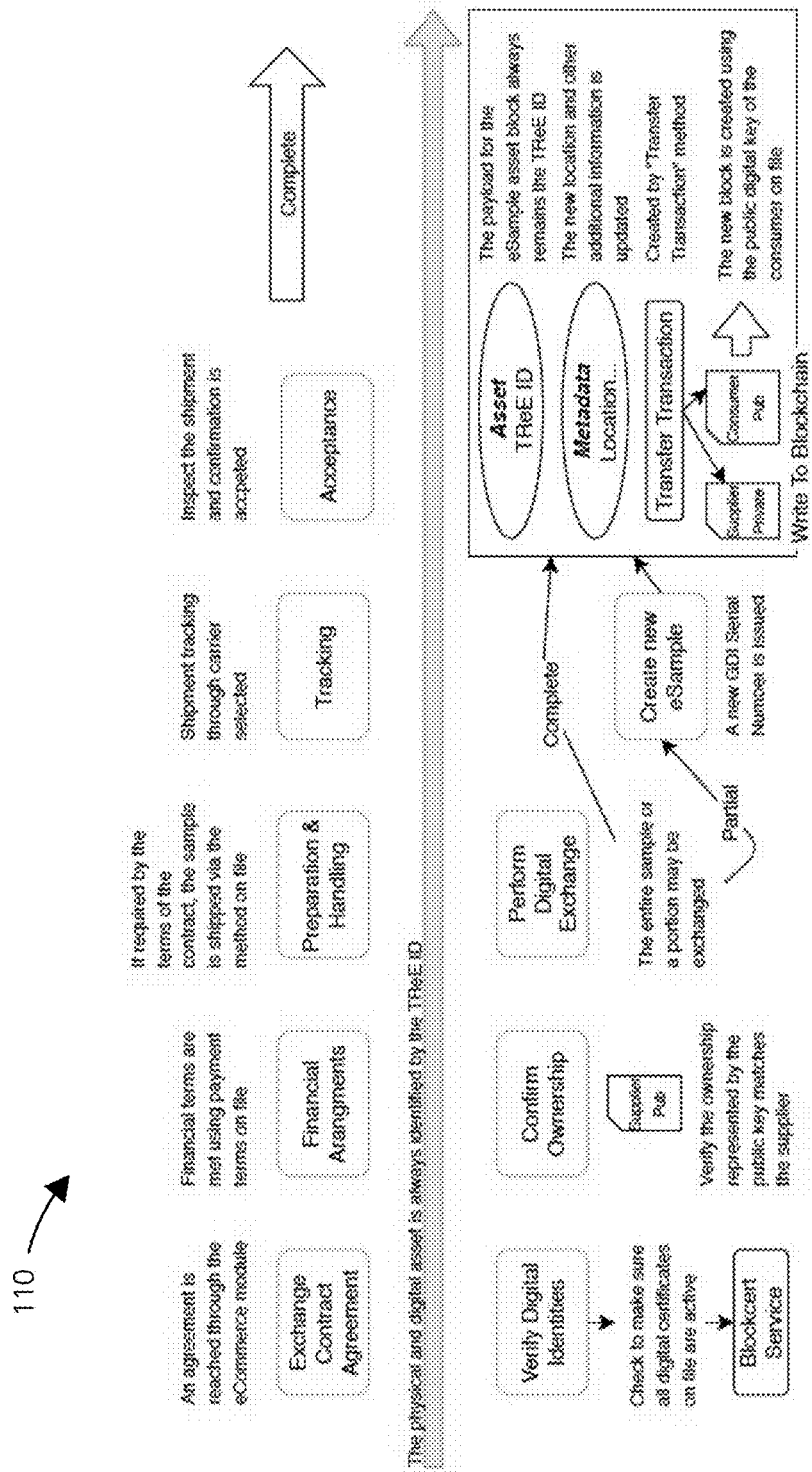
FIG. 11 illustrates physical and digital asset management and exchange transaction brokerage.

FIG. 11 shows two pathways to transact a sample according to the present system and method. The physical and digital assets are identified by the sample's TReE ID, and the physical and digital assets correspond to one another. As alluded to before, and referring to the upper portion or pathway of FIG. 11, an agreement is negotiated between the parties to a transaction or transfer. A formal Exchange contract may be executed, which may be generated and confirmed using modern online digital methods as appreciated by those skilled in the art. The agreement can include financial terms, physical or digital asset handling and delivery terms, shipping and asset tracking terms, insurance terms, return guarantees, or other terms leading to the acceptance of the asset by its new holder (the buyer). Terms for the logistics of the transfer of the physical asset or other terms are likewise agreed in this process, including confirmation of the old (transferor's) address and the new (transferee's) address the specimen will be shipped from and to.

The digital or crypto asset transfer proceeds along the lower pathway of process 110 shown at the bottom of FIG. 11. First, the identities of the transacting parties and the digital asset are verified using public/private key exchange methods. For example, the original owner, holder, supplier or transferor of the assets is confirmed through his or her public key. The digital asset is associated with the same TReE ID as the corresponding physical asset. A Blockcert service may be used to verify identities outside of the Exchange. The digital asset is exchanged in the digital exchange, which may be the entirety of the asset or a sub-sample of the original asset. If the assets are divided into more than one part, the manager of the Exchange issues each sub-divided asset a new serial number which is attached to the sample's parent or original TReE ID to indicate that the sub-samples come from said parent or original sample. The blockchain payload is updated to reflect the transaction in the digital sample.

Figure 12:
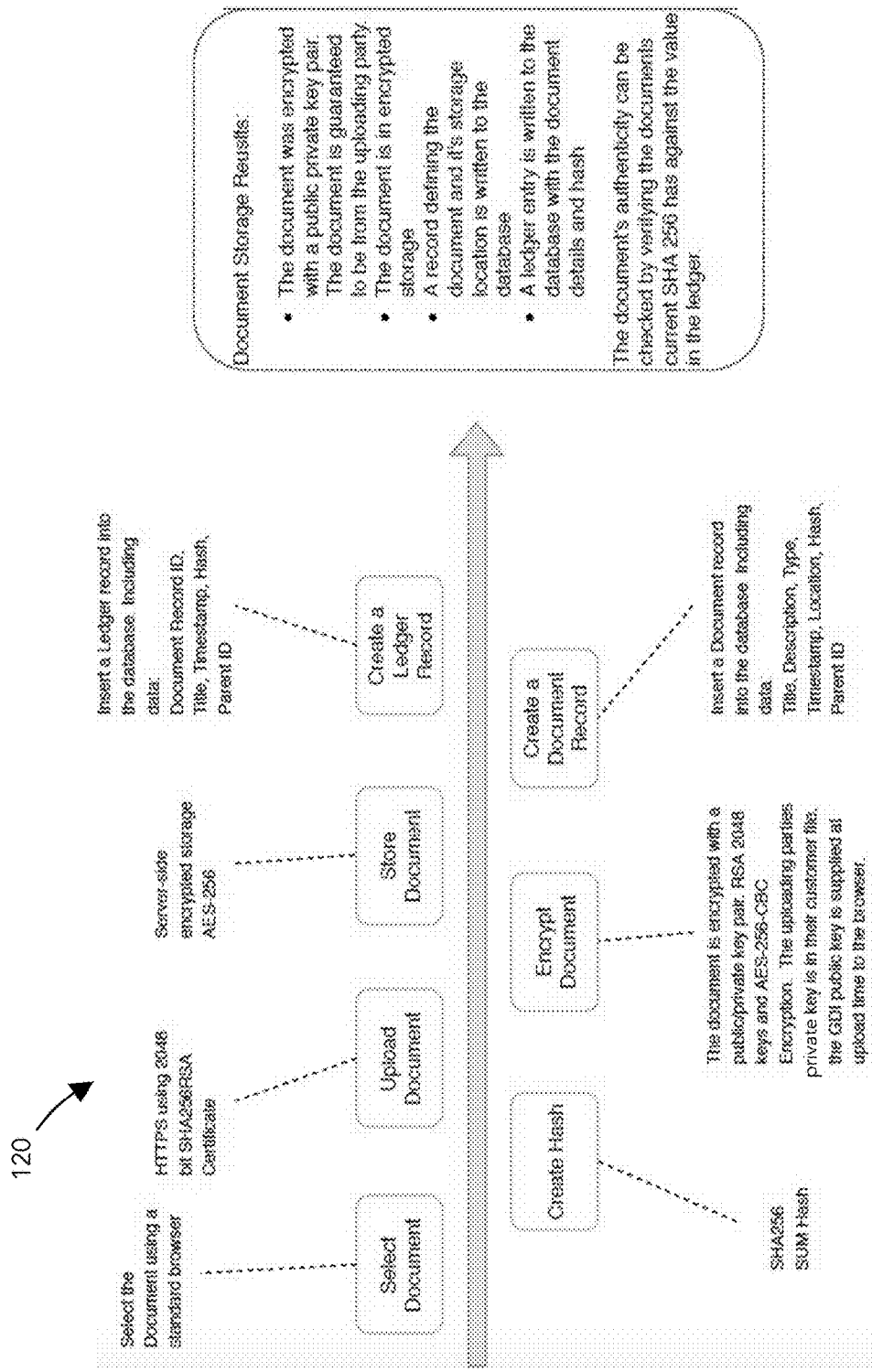
FIG. 12 illustrates processing and management of electronic documents.

Electronic documentation is an integral part of the present process. FIG. 12 illustrates an exemplary process 120 for handling and storing documents according to one or more embodiments. A standard web browser may be used to select a document, e.g., through a user interface thereof. The document is "hashed" using a mathematical model to generate a standard-length hashed result using a private code, for example using the SHA256 method. The document is securely uploaded, for example using HTTPS and a 2048 bit SHA256RSA certificate, which ensures that the document is not altered by an unauthorized party after receipt. The document is encrypted with a public/private key pair, such as using RSA 2048 keys and AES-256-CBC encryption. However, it is to be understood that other encryption methods can be used. The party uploading the document has its private key in their customer file with the operator of the Exchange. The operator of the Exchange also has a public key that is supplied at upload time to the browser. The document is stored on the Exchange operator's server (or other server suitable coupled to said system) and may be server-side encrypted for example using AES-256 or other method. A record of the document is created corresponding to said document. This document record is inserted into the Exchange's database, which includes for example a title, description, type, timestamp, location of the document, hash and parent ID information. Finally, a ledger record is created and inserted into the database, which includes for example a document record ID, a title, a timestamp, a hash and a parent ID.

Having established secure storage of encrypted documents in the present system and method, the present technique thus can guarantee the identity of the party uploading the document (because of the use of the party's public/private key pair); the document is stored in an encrypted manner; a record defining the document and its storage location is written to the database; and a ledger entry is written to the database with the document details and hash. The document's authenticity can be checked by verifying the document's current SHA256 hash against the value in the ledger.

Figure 13:
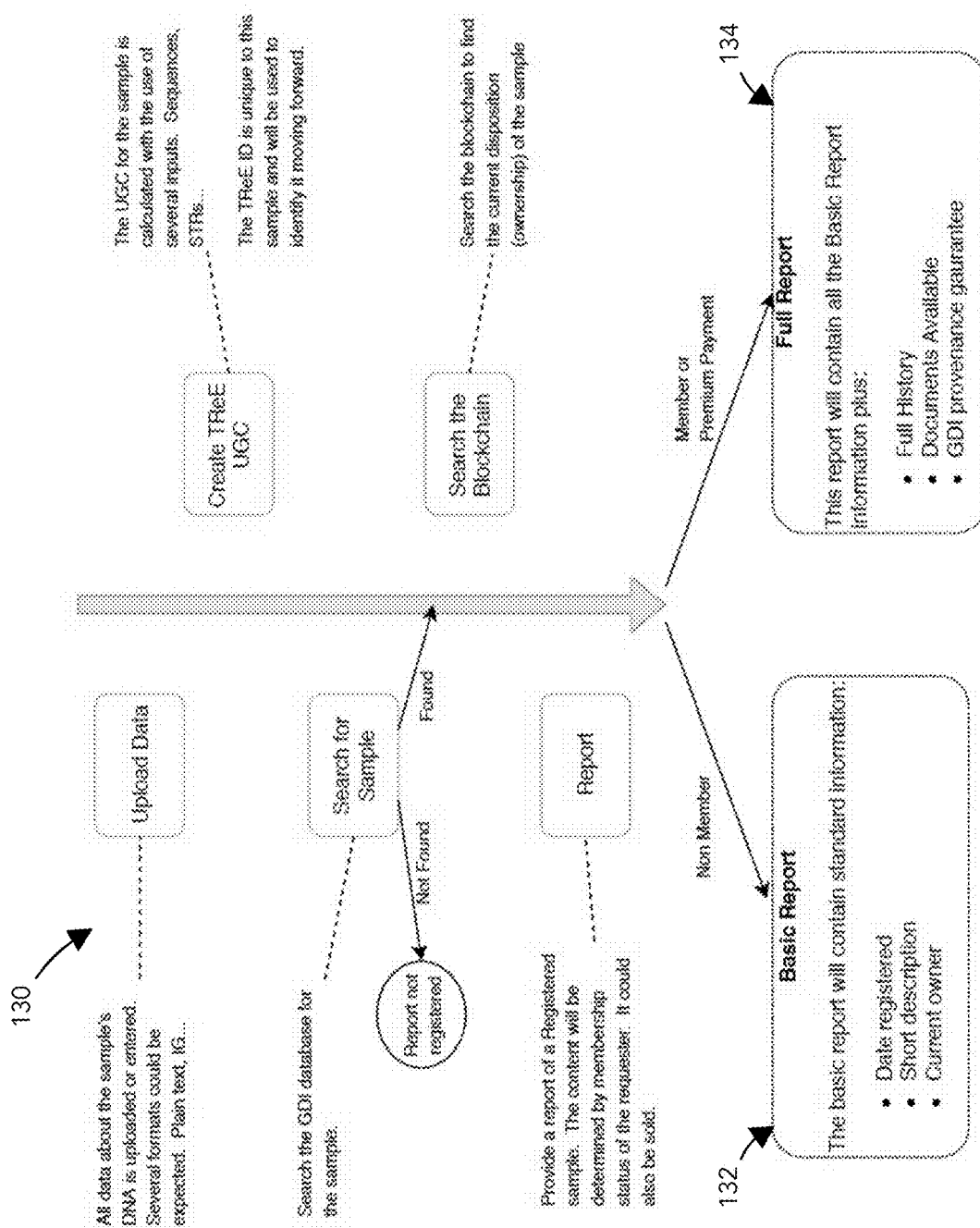
FIG. 13 illustrates basic and full audit report generation.

FIG. 13 illustrates an exemplary process for performing a basic or complete audit according to an aspect. These audits can yield a basic report 132 or a full report 134, respectively. Data is uploaded regarding the sample of interest, including its DNA sequence. This information may be encoded in a variety of formats including plain text or other formats. A UGC and TReE ID are generated for the sample in question, which uniquely identifies the sample as described earlier. The system searches for the sample in the database of the Exchange operator. If a sample with a matching TReE ID is found, the blockchain is searched to locate and identify the current holder or owner of the sample. A report or audit result is generated regarding the sample of interest if the sample is registered in the Exchange. In one example, non-members of the present Exchange could receive a basic report 132 containing, e.g., the sample's registration date, a short description of the sample, and some identification of the sample's owner. In another example, a full report 134 is generated, containing all the basic report information as well as, e.g., a full history of the sample, any available documents relating to the sample, or even a provenance guarantee from the operator of the Exchange. This full report 134 could be provided to premium or paying members of the Exchange. Of course, the description of the audit reports above is merely an example illustrating one or more services available with the present system and method, and is optional and can be eliminated or substituted with equivalent or other services as desired.

Figure 14:
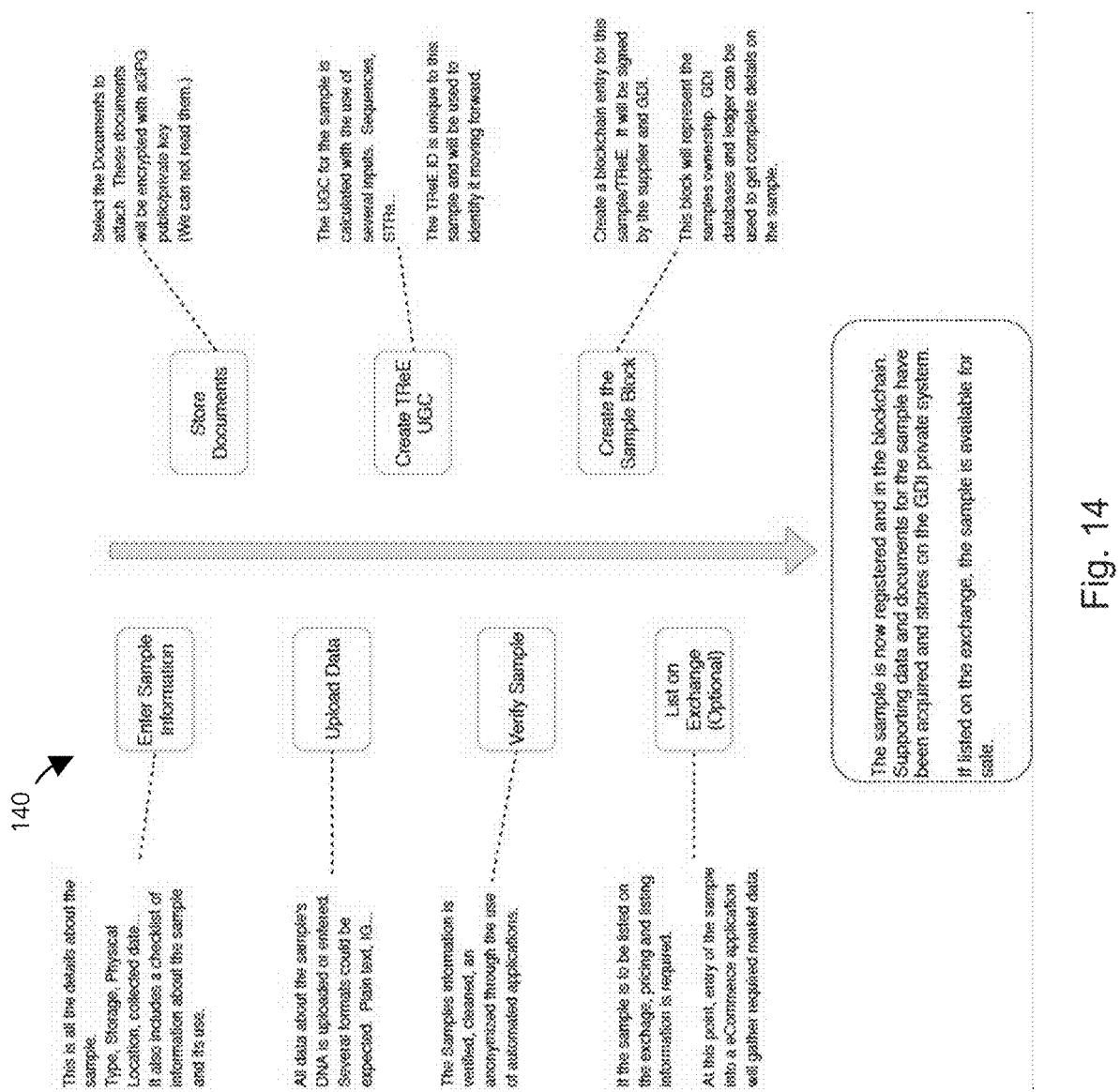
FIG. 14 illustrates the encoding process using a blockchain.

FIG. 14 illustrates an exemplary process 140 for registration of a sample in the blockchain. First, sample information is entered using a sample registration page, including for example the sample's type, physical location, date of collection and other pertinent information about the sample's usage. Documents corresponding to the sample are selected and encrypted with the owner's public/private key pair as discussed before. The documents are uploaded with the sample information. The TReE ID is again computed, as explained earlier, uniquely identifying the sample.

Once uploaded, the information about the sample is verified. The information may be processed or cleaned or anonymized in some embodiments. The sample block is then created for use in the blockchain. The sample's TReE ID or digital asset blockchain entry is signed by the owner/supplier of the sample and by the Exchange operator (sometimes referred to herein as GENERAL DONORS INC. or GDI). This block represents the sample's ownership. The Exchange operator or GDI databases and/or ledger can be used to get complete details about the sample.

The sample, now verified and having its information and documentation securely encoded, is therefore registered and in the blockchain. With the owner's consent, the Exchange operator may now publish and list the sample for sale on the Exchange.

Figure 15:
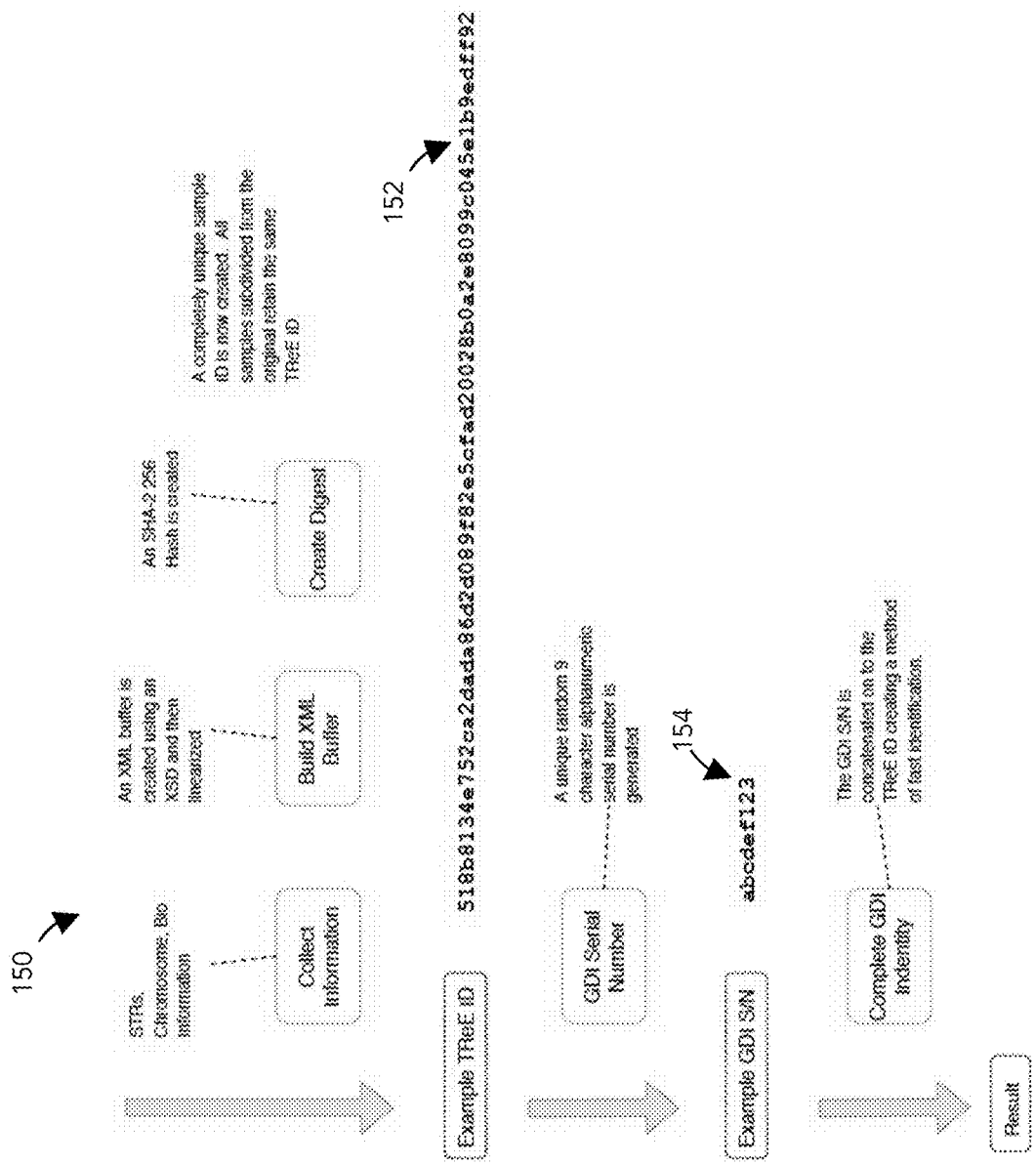
FIG. 15 illustrates generation of unique identifier codes.

FIG. 15 shows a process 150 for creating unique sample identifiers based on the UGC described herein. First, STRs, chromosomes or bio information are collected and encoded into machine-readable data for example that can be processed, stored or transmitted over communication networks. In an example, a XML buffer is created and linearized. A digest is created using a SHA-2 256 hash. This process creates a unique sample identifier based on the genetic code of the sample as stated. Any sub-samples derived from the sample may have this unique genetic code (UGC) as part of its own specific ID, optionally concatenating the original parent sample's UGC to another set of ID data associated with the sub-sample. An example TReE ID is shown at 152 as an illustration.

Additionally, in a non-limiting aspect, a unique random code (e.g., a 9-character alphanumeric serial number) is generated by the Exchange operator, which may be referred to herein as a GDI Serial Number. An example of a GDI Serial Number is shown at 154.

A unique identifier, sometimes referred to herein as the TReE ID can now be defined as the concatenation of both the above UGC as well as the GDI Serial Number. This can be used for identification of the sample. This way, a plurality of sub-samples taken from a parent or original sample may be created and separately uniquely identified even though the sub-samples all share the genetic code of their common parent.

Figure 16:
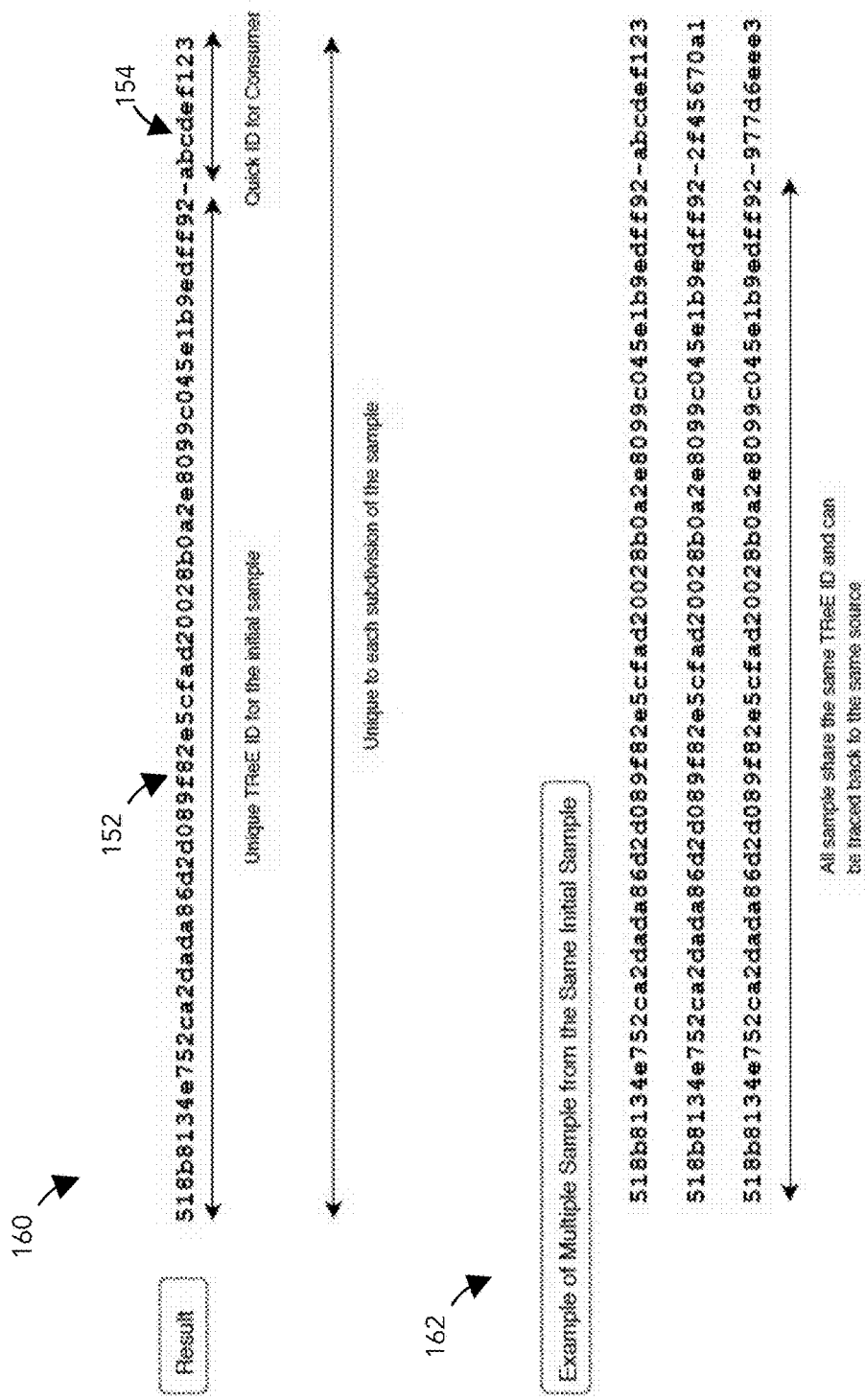
FIG. 16 illustrates combining genetic and serial IDs for a sample or sub-sample.

FIG. 16 illustrates the above unique TReE ID at 160 comprising said UGC 152 and said GDI Serial Number 154. It is to be appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. Variations and modifications of the embodiments described herein, which would occur to persons skilled in the art upon reading the foregoing description, are contemplated by and included in this disclosure.

FIG. 17 illustrates an exemplary input 170 set provided to generate the present TReE ID code identifying a sample. Various information regarding the source of the sample (e.g., sample date, donor's sex, age, race, height, weight) 172 as well as specific aspects of interest about the donor, for example his medical condition 173, are provided. Also, a gene sequence data 174 generated by a sequencing device is also input to the UGC-generation process as described earlier. These are encoded into a TReE Request. Other information, or alternative data can be equally included, deleted or substituted for the shown example in various embodiments as needed.

Figure 18:
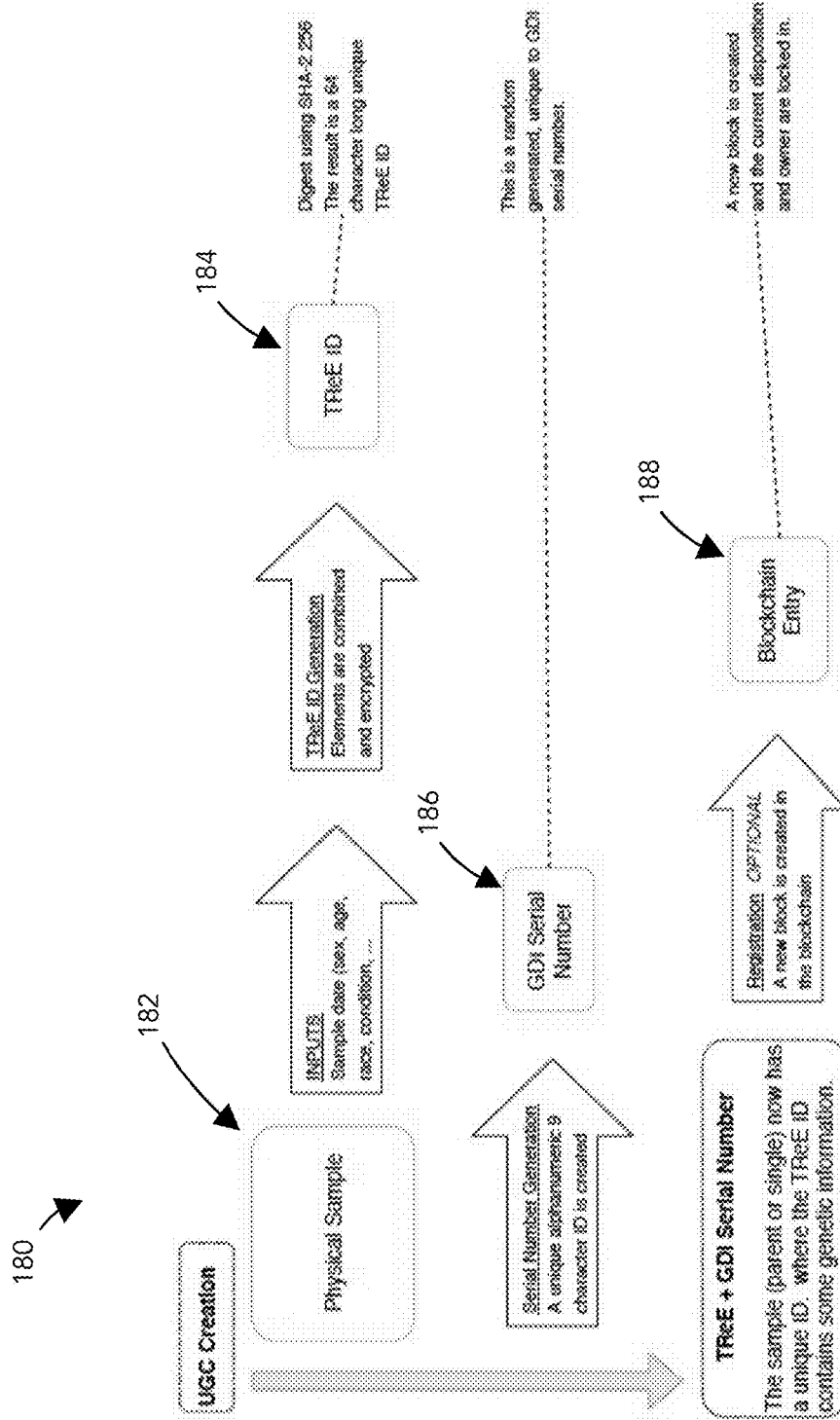
FIG. 18 illustrates processing of unique codes for a sample into a blockchain.
Figure 19:
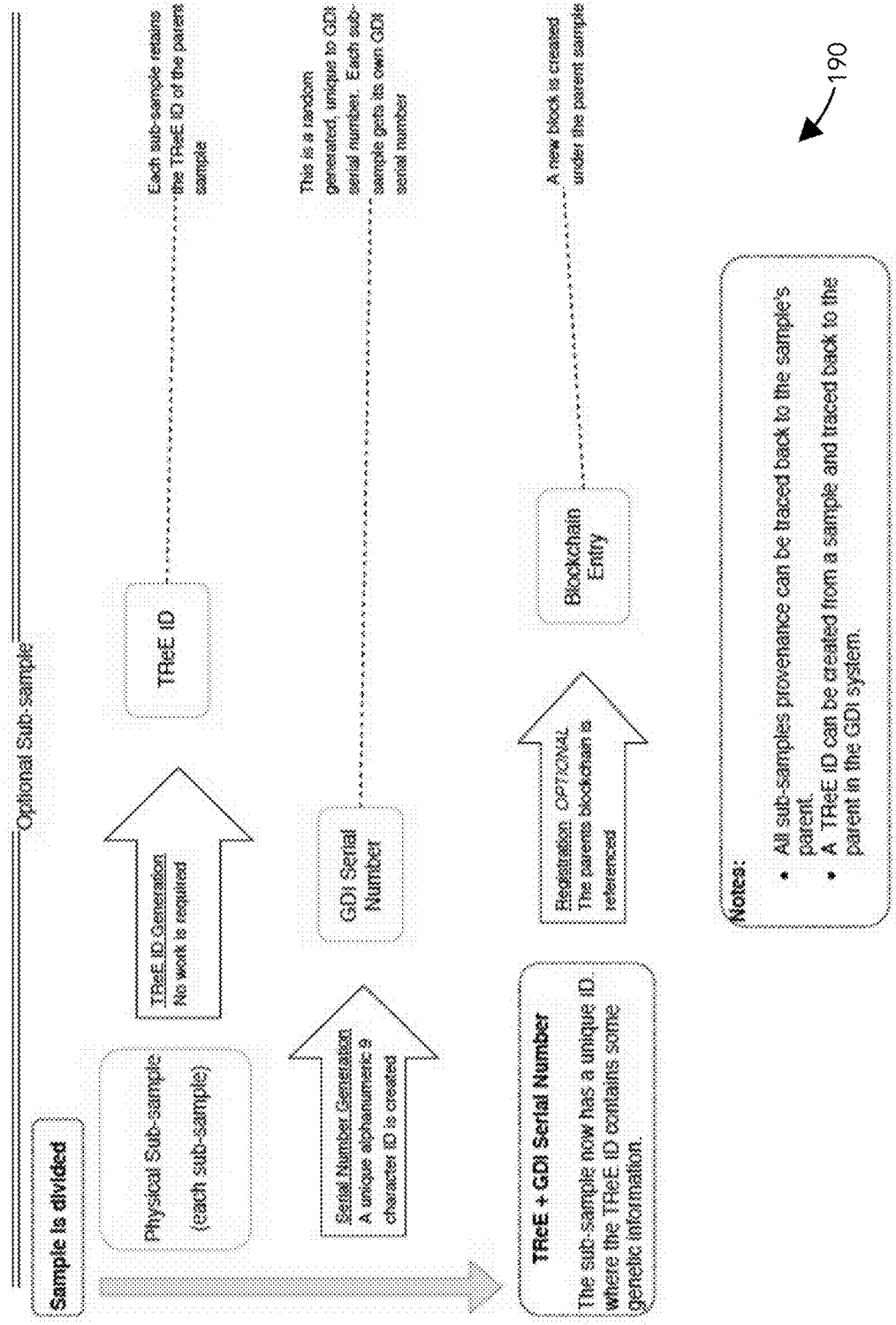
FIG. 19 illustrates processing of unique codes for a sub-sample.

FIGS. 18 and 19 illustrate in more detail some example operations or processes relating to UGC creation and handling in some embodiments.

As mentioned before, a physical specimen or sample 182, which is a physical asset to be used in the present Exchange, is obtained from a source (a donor or existing owner). A TReE ID 184 is created by taking inputs as outlined in the prior figure, including the donor's basic data (sex, age, race, condition . . . ) combined with the genetic sequence information unique to the sample (UGC). These inputs are considered in generating the TReE ID for the sample. This UGC comprises (in an example) a 64 character long unique ID for the sample that can be placed into a digest for use in a blockchain architecture. Furthermore, as explained, the sample Exchange operator can add a unique or random (e.g., 9-character sometimes referred to herein as a GDI Serial Number) serial number to give the sample a unique Fast ID code, which can be the concatenation of the UGC and the GDI Serial Number 186. This allows sub-samples of the parent or original sample to be divided therefrom, each encoded by the parent/original sample's UGC, but also by the sub-sample's unique serial number as well.

In an optional step, the TReE ID is registered in a new block of the blockchain as blockchain entry 188. This block securely encodes the current disposition and owner of the sample (physical asset) and corresponding digital asset.

The steps at 190 are optional procedures for managing such sub-samples obtained from the original parent sample. Sub-samples share the genetic code of the parent, and share its TReE ID, but are further identified by their respective GDI Serial Numbers to distinguish each sub-sample from the other. As before, the sub-samples may be registered in blocks and added to the blockchain.

Figure 20:
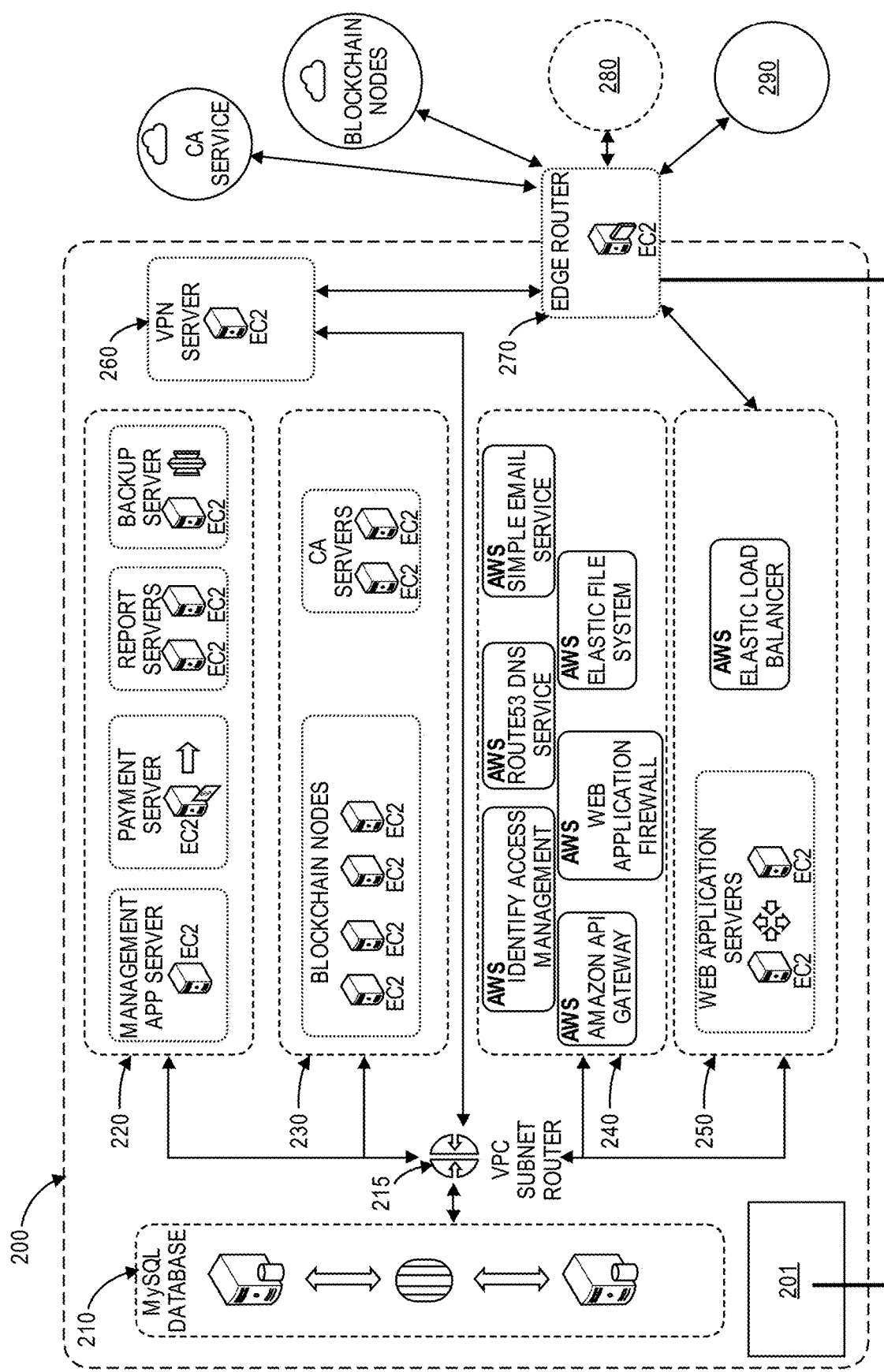
FIG. 20 illustrates an exemplary architecture.

FIG. 20 illustrates an architecture and system 200 used in one or more embodiments. As an architecture and system, the present invention operates to allow and facilitate functions and results not previously known or possible in the art. The design and configuration of the system's hardware and machine-executable instructions and encoded data signals cause said system to deliver the outputs described here using the methods and inputs as described. A sequencing apparatus 201 may be included with system 200 in some embodiments, or separately used in the present context without being included with system 200, as suitable. Therefore, the presently illustrated example should not be considered limiting, as other appropriate configurations falling within the scope of this discussion and appended claims are equally envisioned and possible. The sequencing apparatus 201 would be capable of taking a physical biosample and generating a unique corresponding output signal or encoded data for use in a UGC and subsequent ID, digital asset, and blockchain process as described herein.

A cloud-based architecture 200 may be built on an Amazon Web Services (AWS) platform, with a virtual private cloud (VPC) built thereon that can be owned and/or operated by the present Exchange operator. The system 200 may include a database 210, which can be a MySQL database type or any other that suits the application at hand. Several sub-nets 220, 230, 240, 250 may be implemented and coupled to the other parts of system 200 through a VPC subnet router 215.

One or more embodiments may include an internal services subnet 220 comprising a management app server such as a Tomcat, Angular, Iconic and/or Node.js server; a payment server such as a Monetra or FirstData payment gateway to manage customer payments; one or more report servers such as a Jaspersoft server; and one or more backup servers such as Amazon Glacier Access servers. The various examples given herein are not provided by way of limitation, and other alternative types of servers and technology platforms can be substituted or added to these examples. Also, the various commercially-available components may have trade names provided herein for illustration, which are trademarks of their respective holders.

A blockchain subnet 230 comprises a plurality of blockchain nodes. For example, several nodes may be used to create an initial blockchain or network for the present purposes. One or more certification authority (CA) servers are also coupled to or connected in said blockchain subnet.

Operations are facilitated by a managed services subnet 240 such as an AWS managed services network providing identity access management, API gateway services, web application firewall, DNS services, email services, and elastic file systems, among other support services.

A web application subnet 250 includes one or more web application servers such as AWS AutoScale Group servers running a suitable software base such as Tomcat, Angular, Ionic or Node.js software. An AWS elastic load balancer or similar system may be employed as well, as appropriate for a given purpose.

The system 200 may also contain, in one or more embodiments, a virtual private network (VPN) server 260 such as an Active Server, OpenVPN, etc. as well as an edge router 270, which may run a VyOS or similar program to provide NAT, ACL, firewall or other functionality when coupled to an open data network such as the internet 280.

Customers, members, clients or generally users 190 of the system 200 access the system by way of a client device of their own, suitably equipped and communicating through edge router 270. CA services, other blockchain nodes, and other parties can likewise exchange data and blockchain blocks, etc. with system 200 through edge router 270 or a similar means.

It can thus be seen from the discussion and examples above that the present applicant provides a novel and useful system and method. The system and method include structural and architectural designs implemented in computing, data storage, processing, genetic sequencing machinery, and communication machinery. In an aspect, said machinery forms an apparatus or group of apparati that individually and collectively, especially when configured with the present software instruction sets and data, act on certain input signals encoding input information so as to generate new and useful output signals encoding output information to achieve an actual and new secure authenticated and scalable exchange for genetic-based materials such as biosamples.

Specifically, this invention and its embodiments are configured and arranged to provide a unique genetic code (UGC) and TReE ID corresponding to a biosample, for example by encoding and combining information generated by a gene sequencing apparatus hereof or coupled hereto. In addition, this system and method can combine such genetic codes with other unique or random serial number information to provide (e.g., through concatenation) a unique fast ID such as the TReE ID that not only comprises the UGC data but also the serial number data so that one or more parent and/or sub-sample or child samples can be derived from the parent and have respective unique identification means. The system and method thus generate, in addition to the physical asset (sample), a corresponding digital asset encoding information, including the genetic code information, of the sample of interest.

An exchange for biomaterials and samples relying on encryption and blockchain architectures is therefore enabled. The exchange can include databases for securely housing the encrypted blocks, certificates and documents and other digital assets corresponding to the physical assets of interest. The exchange securely and with ability to verify source, destination and nature of both the physical and digital assets, allows for a sale, transfer or other transaction in the assets (physical and digital).

An asset pair comprising both the physical biosample asset and its corresponding digital asset are therefore provided for use in the exchange. eCommerce methods can be used to list, advertise, search for and otherwise transact in the asset pair.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein. The present materials, methods, and examples are illustrative only and not intended to be limiting.

What is claimed is:

1. A method for secure transactions in a biosample, comprising:
   identifying a physical asset comprising said biosample;
   obtaining information regarding said biosample from a provider of said biosample;
   encoding the information regarding said biosample into a corresponding sample data set;
   interrogating said biosample using a sequencing machine to generate a short tandem repeat (STR) code corresponding to said biosample;
   generating a digital asset uniquely corresponding to said physical asset comprising a unique genetic code (UGC) based at least on said STR and said sample data set;
   recording said UGC in a secure data store;
   generating a UGC-codified hash using a public-private key method;
   encoding said digital asset into a first block of a blockchain;
   brokering, in an exchange platform, a transaction in both the physical asset and its corresponding digital asset between a first party who holds rights in said physical and digital assets and a second party who intends to take rights in said physical and digital assets following the transaction; and
   encoding said transaction, following its completion, into a second block of said blockchain.

2. The method of claim 1, further comprising generating a sample serial number for said sample, wherein generating the digital asset is further based on said sample genetic code and STR expression profile.

3. The method of claim 2, further comprising dividing said biosample into a plurality of sub-samples, each of which is assigned its own different respective serial number, and generating a unique digital asset corresponding to each such sub-sample at least based on said STR and the respective serial number of each sub-sample.

4. The method of claim 1, further comprising brokering the transfer of said physical sample from the first party to the second party.

5. The method of claim 1, further comprising encrypting said digital asset using a private key of said first party and public key of said second party.

6. The method of claim 1, wherein the sample data set includes a characteristic of said donor.

7. An architecture for secure transactions in a biosample, comprising:
   a genetic testing apparatus for interrogating a physical asset comprising said biosample to output a unique short tandem repeat (STR) code corresponding to said biosample;
   a secure network of servers, configured and arranged to exchange encoded data in signals passed along one or more communication pathways coupling said servers;
   one or more servers coupled to said network being configured and arranged to receive a sample data set describing said biosample and to receive said STR code, register said sample data set and STR code into a data store coupled to the first server, and process said STR code and said sample data set to generate a digital asset comprising a unique genetic code (UGC) corresponding to said biosample; and a wide area network interface coupled to said network configured and arranged to provide access to at least a first and second user and further configured and arranged to broker a transaction between said first and second users in said physical and digital assets.

8. The system of claim 7, further comprising a blockchain block generator that is configured and arranged to take said digital assets and securely encode the same into a block, and delivering said block into a blockchain accessible over said network to a plurality of blockchain nodes.

\* \* \* \* \*